(12) United States Patent
Liu

(10) Patent No.: US 7,300,639 B2
(45) Date of Patent: Nov. 27, 2007

(54) PROCESS FOR REMOVING METALS FROM LIQUIDS

(75) Inventor: Wansheng Liu, Edison, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 525 days.

(21) Appl. No.: 10/726,076

(22) Filed: Dec. 2, 2003

(65) Prior Publication Data

US 2004/0170547 A1    Sep. 2, 2004

Related U.S. Application Data

(60) Provisional application No. 60/430,416, filed on Dec. 3, 2002.

(51) Int. Cl.
| C07F 15/00 | (2006.01) |
| C01G 53/00 | (2006.01) |
| C07D 231/10 | (2006.01) |

(52) U.S. Cl. .................. 423/139; 556/16; 548/252; 548/341.1

(58) Field of Classification Search ............... 548/252, 548/341.1
See application file for complete search history.

(56) References Cited

U.S. PATENT DOCUMENTS

| 3,656,939 A | 4/1972 | Boehm et al. |
| 4,664,700 A | 5/1987 | Alexandratos |
| 4,952,321 A | 8/1990 | Bradshaw et al. |
| 5,061,773 A | 10/1991 | Panster et al. |
| 5,458,787 A | 10/1995 | Rosin et al. |
| 5,695,882 A | 12/1997 | Rosenberg |
| 5,997,748 A | 12/1999 | Rosenberg et al. |
| 6,232,262 B1 | 5/2001 | Sielcken et al. |
| 6,291,722 B1 | 9/2001 | Li |

FOREIGN PATENT DOCUMENTS

| DE | 107372 | 1/1899 |
| EP | 0 028 392 | 2/1983 |
| EP | 0 285 218 | 12/1994 |
| JP | 52-126685 | 10/1977 |
| JP | 53-6296 | 1/1978 |
| JP | 53-67619 | 6/1978 |
| JP | 53-67620 | 6/1978 |
| JP | 59-133389 | 7/1984 |
| JP | 60-50193 | 3/1985 |
| JP | 1-128533 | 5/1989 |
| JP | 3-199392 | 8/1991 |
| WO | WO 94/29226 | 12/1994 |
| WO | WO 96/09985 | 4/1996 |
| WO | WO 00/59506 | 10/2000 |

OTHER PUBLICATIONS

Agris, C.H. et al., "Inhibition of Vesicular Stomatitis Virus Protein Synthesis and Infection by Sequence-Specific Oligodeoxyribonucleoside Methylphosphonates", Biochemistry, vol. 25, No. 20, pp. 6268-6275 (1986).

Anderson, N.G. et al., "Process Development of 5-Fluoro-3-[3-[4-(5-methoxy-4-pyrimidinyl)-1-piperazinyl] propyl]-1 *H*-indole Dihydrochloride", Organic Process Research & Development, vol. 1, No. 4, pp. 300-310 (1997).

Baba, Y. et al., "Extraction Equilibria of Palladium(II) and Platinum(IV) with Di(2-ethylhexyl)aminophosphonic acid from Acidic Chloride Media", Solvent Extraction Research and Development, Japan, vol. 2, pp. 93-101 (1995).

Cazenave, C. et al., Chapter 3: "Antisense Oligonucleotides", Antisense Nucleic Acids and Proteins: Fundamentals and Applications, Marcel Dekker, Inc., publ., Mol, J.N.M. et al., eds., pp. 47-93 (1991).

Chung, D.-Y. et al., "Formation of Palladium Precipitate by Hydrazine in a Simulated High Level Liquid Waste", Journal of Radioanalytical and Nuclear Chemistry, Articles, vol. 204, No. 2, pp. 265-274 (1996).

Collier, A.C. et al., "Combination therapy with zidovudine, didanosine and saquinavir", Antiviral Research, vol. 29, p. 99 (1996).

Crooke, R.M., "In vitro toxicology and pharmacokinetics of antisense oligonucleotides", Anti-Cancer Drug Design, vol. 6, pp. 609-646 (1991).

De Mesmaeker, A. et al., "Antisense Oligonucleotides", Acc. Chem. Res., vol. 28, pp. 366-374 (1995).

(Continued)

*Primary Examiner*—Kamal A. Saeed
(74) *Attorney, Agent, or Firm*—Maureen P. O'Brien

(57) ABSTRACT

A process is provided for removing one or more metals from liquids. Also provided is a process for the synthesis of aP2 inhibiting compounds having the formula (I)

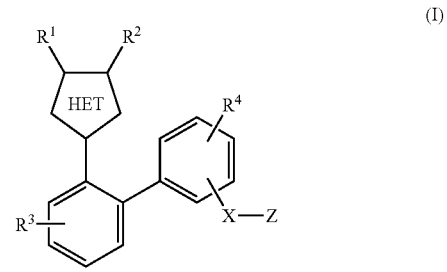

wherein $R^1$, $R^2$, $R^3$, $R^4$, HET, and X-Z are as described herein, which process comprising the step of removing one or more metals from a solution of the compound of formula I or an intermediate or precursor thereof. The processes for removing metal comprise the step of contacting the liquid with a solid extractant comprising a metal-binding functionality.

28 Claims, No Drawings

OTHER PUBLICATIONS

Diels, L. et al., "The use of bacteria immobilized in tubular membrane reactors for heavy metal recovery and degradation of chlorinated aromatics", Journal of Membrane Science, vol. 100, pp. 249-258 (1995).

Foersterling, H.-U., "Investigations of the Adsorption of Palladium on Carbonaceous Adsorberts Modified with Dimethylglyoxime—1. The Adsorption of Dimethylglyoxime on Selected Carbonaceous Adsorbents", Carbon, vol. 28, No. 1, pp. 27-34 (1990).

Ghosh, A.K. et al., "Nonpeptidal $P_2$ Ligands for HIV Protease Inhibitors: Structure-Based Design, Synthesis, and Biological Evaluation", J. Med. Chem., vol. 39, No. 17, pp. 3278-3290 (1996).

Hodgson, C.P., "The Vector Void in Gene Therapy: Can viral vectors and transfection be combined to permit safe, efficacious, and targeted gene therapy?", Bio/Technology, vol. 13, pp. 222-225 (1995).

Ishihara, K. et al., "Removal of Palladium(II) from Aqueous and Organic Solutions by Polystyrene-bound Trimercaptotriazine", Chemistry Letters, pp. 1218-1219 (2000).

Jiang, L. et al., "Study on the Extraction Separation of Rh from Pt, Pd, Ir by Radiotracer Method—Purification of Rh", He Huaxue Yu Fangshe Huaxue (Journal of Nuclear and Radiochemistry), vol. 8, No. 2, pp. 108-112 (1986) (with English abstract).

Kabanov, A.V. et al., "A new class of antivirals: antisense oligonucleotides combined with a hydrophobic substituent effectively inhibit influenza virus reproduction and synthesis of virus-specific proteins in MDCK cells", FEBS Letters, vol. 259, No. 2, pp. 327-330 (1990).

Kabanov, A.V. et al., "New approaches to targeting bioactive compounds", Journal of Controlled Release, vol. 28, pp. 15-35 (1994).

Makita, Y. et al., "Single-pole electrolysis cell and electrolysis using this cell", Chemical Abstracts, vol. 115, No. 17573e, pp. 599-600 (1991).

Maryanoff, C.A. et al., Chapter 18: "Catalysis from the Perspective of an Organic Chemist: Common Problems and Possible Solutions", Catalysis of Organic Reactions, Marcel Dekker, Inc., publ., Rylander, P.N. et al., eds., pp. 359-379 (1988).

Masri, M.S. et al., "Chemical Modification of Insoluble Polymers for Certain End Uses", Polymer Preprints: Papers presented at Chicago meeting, Division of Polymer Chemistry, Inc., American Chemical Society, vol. 16, No. 2, pp. 70-75 (1975).

Milligan, J.F. et al., "Development of Antisense Therapeutics: Implications for Cancer Gene Therapy", Gene Therapy for Neoplastic Diseases, Annals of the New York Academy of Sciences, vol. 716, The New York Academy of Sciences, New York, NY, publ., Huber, B.E. et al., eds., pp. 228-241 (1994).

Mimura, H. et al., "Selective Separation of Palladium by Insoluble Ferrocyanide-Alginate Composites", Tohoku Daigaku Sozai Kogaku Kenkyusho Iho, vol. 56, pp. 1-8 (2000) (with English abstract).

Nogami, M. et al., "Ion-Exchange Selectivity of Tertiary Pyridine-Type Anion-Exchange Resin for Treatment of Spent Nuclear Fuels", Nuclear Technology, vol. 115, pp. 293-297 (1996).

Pearson, R.G., "Hard and Soft Acids and Bases", Journal of the Americal Chemical Society, vol. 85, No. 22, pp. 3533-3539 (1963).

Pearson, R.G., "Hard and Soft Acids and Bases, HSAB, Part I: Fundamental principles", Journal of Chemical Education, vol. 45, No. 9, pp. 581-587 (1968).

Pearson, R. G., "Hard and Soft Acids and Bases", Copyright 1973, Dowden, Hutchinson & Ross, Inc., Strousdburg, Pennsylvania.

Radová, Z. et al., "Sorption of Pd(II) from Aqueous Solutions of Chlorocomplexes by the Copolymer of Glycidylmethacrylate and Ethylenedimethacrylate Modified with Ethylenediamine. The Structure of Complexes", Die Angewandte Makromolekulare Chemie, vol. 81, pp. 55-62 (1979).

Raskin, I. et al., "Method for removing soluble metals from an aqueous phase", Chemical Abstracts, vol. 122, No. 169223y, p. 586 (1995).

Rosso, V.W. et al., "Removal of Palladium from Organic Reaction Mixtures by Trimercaptotriazine", Organic Process Research & Development, vol. 1, No. 4, pp. 311-314 (1997).

Shukla, J.P. et al., "Selective Solvent Extraction of Palladium (II) with Thiacrowns from Aqueous Chloride/Nitrate Reprocessing Waste Solutions", Nuclear Science Journal, vol. 33, No. 1, pp. 39-51 (1996).

Stull, R.A. et al., "Antigene, Ribozyme and Aptamer Nucleic Acid Drugs: Progress and Prospects", Pharmaceutical Research, vol. 12, No. 4, pp. 465-483 (1995).

Suyama, K. et al., "A New Biomaterial, Hen Egg Shell Membrane, to Eliminate Heavy Metal Ion from Their Dilute Waste Solution", Applied Biochemistry and Biotechnology, vol. 45/56, pp. 871-879 (1994).

Suyama, K. et al., "Biosportion of Precious Metal Ions by Chicken Feather", Applied Biochemistry and Biotechnology, vol. 57/58, pp. 67-74 (1996).

Wei, Y.-Z. et al., "Adsorption and Elution Behavior of Platinum-Group Metals in Nitric Acid Medium", Ion Exchange Developments and Applications, vol. 182, pp. 174-181 (1996).

Wen, D. et al., "Study on magnetic chelating resin. II. Preparation of PSE2 and its adsorption properties to metal ions", Chemicals Abstracts, vol. 123, No. 3418261, p. 66 (1995).

Yordanov, A.T. et al., "Solvent extraction of divalent palladium and platinum from aqueous solutions of their chloro complexes using an $N,N$-dimethyldithiocarbamoylethoxy substituted calix[4]arene", Inorganica Chimica Acta, vol. 240, pp. 441-446 (1995).

Zuo, G. et al., "Extraction of Noble Metals by Sulfur-Containing Reagents and Solvent Impregnated Resins", Solvent Extraction and Ion Exchange, vol. 13, No. 5, pp. 879-899 (1995).

De, A. K., "Solvent Extraction of Metals", Van Nostrand Reinhold Company Ltd., New York, 1970.

PROCESS FOR REMOVING METALS FROM LIQUIDS

This application claims priority to U.S. Provisional Application Ser. No. 60/430,416 filed Dec. 3, 2002 the entirety of which is incorporated herein by reference.

BACKGROUND OF THE INVENTION

This invention relates to the field of purification of liquids, and specifically to the purification of liquids by the removal of metals therefrom.

It is well known that exposure to certain metals and metal-containing substances causes a variety of ill effects on health. Such exposure occurs by inhalation, ingestion, injection, or any other means through which people and other organisms come into contact with metals or metal-containing substances. Substantial benefits would therefore accrue from the removal of metals from certain substances in order to minimize the harmful effects of metal exposure on people and other organisms.

The deleterious effects of metal exposure range from the temporary respiratory irritation that can result from inhaling an inert metal powder to more serious effects including skin rashes, asthma, allergies and sensitization, headaches, nausea and vomiting, changes in blood pressure and/or heart rate, damage to the heart, damage to the kidneys and/or liver, neurological damage, anemia, and reproductive disorders. Some metals, such as chromium (VI), are well-known mutagens, teratogens, and/or carcinogens. Some metals, such as radium and plutonium, are hazardous because of their radioactivity. Exposure to certain metals, such as arsenic or thallium, can be fatal.

In addition, some metals are known to bio-accumulate. That is, the exposed organism has no mechanism, or only inefficient mechanisms, for excreting the metal. As a consequence, the metal remains in the organism at a level that increases with each additional exposure. Mercury is one well-known bio-accumulating toxic metal.

Aside from health and environmental concerns, there may be other reasons for rendering a particular substance free of metals. For example, the efficient recovery of precious metals is an economically beneficial goal. Also, the presence of paramagnetic or colored metals might interfere with the spectroscopic or spectrophotometric analysis of other materials.

Palladium is a metal that is commonly used in redox catalysis. Palladium-mediated cross-couplings are also of great significance in the synthesis of organic compounds, because such reactions are highly versatile and represent an important means of carbon-carbon bond formation. Palladium containing catalysts may be homogeneous, i.e., soluble in the reaction medium, or heterogeneous. Heterogeneous catalysts may be bulk metals, alloys, or compounds. Heterogeneous palladium catalysts may also comprise a thin layer of active metal, alloy, or compound on a solid support. Other heterogeneous catalysts include palladium bound to one or more ligands immobilized on a solid support. See, e.g., U.S. Pat. No. 6,232,262.

The products of palladium catalyzed or mediated reactions, however, may require further reactions or processing with which residual palladium would interfere. Alternatively, the products may be organic compounds such as drug substances, which, if containing palladium when administered, could cause the patient to be exposed to a heavy metal with potentially toxic effects. Therefore, a particular need exists for efficient processes to remove palladium from organic compounds and liquids containing organic compounds, e.g., the reaction media in which they are produced.

Many methods have been developed to reduce the level of residual palladium in organic processes. The removal of even small amounts of palladium can pose difficulties, however. The traditional approach to removing impurities, that is, selective crystallization of the organic product, often fails to reduce palladium to the level of parts per million, which is highly desirable or even essential for the preparation of drug substances.

One generally applicable strategy is to use the smallest amount of palladium possible in the reaction mixture, thus decreasing the total amount of palladium to be removed from the final product. Another general approach is to re-position palladium catalyzed reactions from the final steps to the earlier steps in the synthetic sequence. The idea behind this strategy is that the processing of subsequent intermediates will reduce the level of residual palladium in the final product, if for no other reason than dilution alone. (Maryanoff, C. A., et al., in *Catalysis of Organic Reactions*; Rylander, P. N., Greenfield, H., Augustine, R. L., Eds.; Marcel Dekker, New York, 1988; pp 368-375; Anderson, N. G., et al. *Org. Process Res. Dev.* 1997, 1, 300.) Electrolytic plating is another commonly practiced method of removing palladium from liquids.

Other approaches for palladium removal can be divided into two categories: extraction and precipitation treatments, and solid phase treatments. The chemistry of the extraction of metals into organic solvents using, e.g., β-hydroxy ketones, 8-hydroxyquinoline, 8-mercaptoquinoline, oximes, hydroxylamines, sodium diethyldithiocarbamate, and others has been reviewed extensively. (De, A. K., et al. *Solvent Extraction of Metals*; Van Nostrand Reinhold Company: New York, 1980.) Trimercaptotriazine (TMT) has also been used to remove palladium from organic reaction mixtures. (Rosso, V. W., et al., *Org. Proc. Res. Dev.*, 1997, 1, 311-314.)

Other examples of methods of removing palladium by extraction from a liquid medium include the use of ligands such as amines, aniline, pyridine, ethylenediamine tetraacetic acid, carboxylates, cyanides, thiocyanates, acetylacetonates, N,N-diethyl-dithiocarbamic acid and the like, triaryl phosphines, and bidentate phosphines (Van Broekhoeven, EP 028392; Pino et al., EP 0285218); N,N-dimethyldithiocarbamoylethoxy-substituted calix[4]arene (Yordanov, A. T., et al. *Inorg. Chim. Acta* 1995, 240, 441.); sulfur-based ligands, e.g., nonylthiourea, dodecylthiourea, triisobutylphosphine sulfide, and thiocrown ethers (Zuo, G.; Muhammed, M. *Solvent Extr. Ion Exch.* 1995, 13 (5), 879; Shukla, J. P., et al. *Nucl. Sci. J.* 1996, 33 (1), 39.); TOA-kerosin (Lingen, J., et al., *He Huaxue Yu Fangshe Huaxue*, 1986, 8(2), 108-112); and [[N,N-bis(2-ethyl-1-hexyl)amino]methyl]phosphonic acid (Baba, Y., et al. *J. Solvent Extr. Res. Dev., Jpn.* 1995, 2, 93.). Hydrazine is a highly effective reagent for the precipitation of palladium from a nitric acid solution. (Chung, D. Y., et al. *J. Radioanal. Nucl. Chem. Articles* 1996, 204(2), 265.)

Some of the solid phase treatments for the removal of palladium from a liquid medium are quite simple, for example, physical separation by filtration. Such an approach would be especially effective for removing precipitates or heterogeneous catalysts from solution.

Non-selective adsorption of impurities, e.g., filtration through activated carbon, is another commonly practiced solid phase treatment. See, e.g., Japanese Patent No. 53067619. In some cases, the activated carbon has been used in combination with other solids, for example, iron sulfide, silica gel, diatomaceous earth, or polyacrylamide (Japanese Patent No. 52126685). Activated carbons modified with dimethylglyoxime (Foersterling, H.-U., *Carbon,* 1990, 28, 27-34.) or with alpha-dioxime (Japanese Patent No. 53067620) have also been used to sequester palladium.

Other solid phase treatments include iminodiacetic acid resins, which selectively bind divalent cations. For example, Chelex 100, a resin available from Bio-Rad Laboratories in Richmond, Calif., has a greater affinity for palladium (II) than for copper (II) in acetate buffer (pH=5). See also German Democratic Republic Patent No. 107372 and Japanese Patent Nos. 03199392, 53006296, 59133389, and 60050193. The macroreticular cation exchange resin Dowex M-33, available from the Dow Chemical Co. of Midland, Mich., is also known to have a high affinity for palladium (II), as does Deloxan THP II, a thiourea-modified resin available from the Degussa Corporation of Parsippany, N.J. Polystyrene-bound trimercaptotriazine (TMT) has been used for like purposes (Ishihara, K., et al., *Chem. Lett.,* 2000, 10, 1218), as has an insoluble aminoalkyl-substituted organopolysiloxane thiourea (U.S. Pat. No. 5,061,773). An ethylenediamine-modified macroporous copolymer of glycidylmethacrylate and ethylenedimethacrylate was used by Radova et al. to remove palladium (II) from aqueous HCl and KCl solutions. *Angew. Makromol. Chem.,* 1979, 81, 55-62.

Anion exchange resins have also been used for the removal of metals, including palladium, from liquids. See, e.g., U.S. Pat. No. 3,656,939. An anion exchange resin containing benzimidazoles and quaternary benzimidazolium species has been used to remove palladium ions from nitric acid solutions. (Wei, Y. Z., et al. *Spec. Publ.-R. Soc. Chem.* 1996, No. 182 (Ion Exchange Developments and Applications), 174.) A tertiary pyridine type anion exchange resin was shown to have a good affinity for palladium under acidic conditions. (Nogami, M., et al., *Nucl. Technol.* 1996, 115, 293.)

Other solids used in the removal of palladium include carbonaceous pyropolymers, which are known to remove palladium from aqueous solutions by reducing palladium ions, thereby plating palladium metal onto the pyropolymer itself. (Rosin, R. R.; Schwerin, W. C., U.S. Pat. No. 5,458, 787; Makita, Y., et al. Japanese Patent JP 89-128533 (*Chem Abstr.* 1991, 115, 17573e).) A magnetic chelating resin with a high content of sulfur and nitrogen atoms was shown to be effective for the removal of palladium ions under acidic conditions. (Wen, D. et al., *J. Wuhan Univ. Technol., Mater. Sci, Ed.* 1994, 9, 54; *Chem. Abstr.* 1995, 123, 341826.) Chromatography on silica gel has been used to remove spent palladium (0) catalyst from reaction mixtures (U.S. Pat. No. 6,291,722). Palladium has been removed by contact with silica gel or other solids whose surfaces have been silanized, then aminated, before functionalization with a variety of palladium binding moieties, such as carboxylates, thiols, amines, imines, phosphines, thiocyanates, isothiocyanates, cyanates, and isocyanates. (U.S. Pat. Nos. 5,695,882 and 5,997,748.) A chemically active ceramic composite material containing thiol and amine moieties is known to remove metal ions from solution. (Tavlarides, L. L.; Deorkar, N., PCT Int. Appl. WO9609985 A1.) Composites of calcium alginate polymer gels with copper ferrocyanide selectively adsorbed palladium (II) from solutions designed to simulate radioactive waste. (Mimura, H., et al., *Tohoku Daigaku Sozai Kogaku Kenkyusho Iho,* 2000, 56, 1-8.)

Several methods of removing palladium through the use of abundant and economical solid biomaterials have also been developed. The chicken feather, an intricate network of stable, water insoluble protein fibers with high surface area, is one such useful biomaterial. It has been reported that chicken feathers can absorb an amount of palladium equal to 7% of their dry weight. (Suyama, K. et al. *Appl. Biochem. Biotechnol.* 1996, 57/58 (Seventeenth Symposium on Biotechnology for Fuels and Chemicals, 1995), 67.) Bacteria immobilized in a tubular membrane reactor have also been used to recover palladium. (Diels, L., et al., *J. Membr. Sci.* 1995, 100, 249.) Other biomaterials useful in palladium removal include chicken eggshell membrane (Suyama, K. et al. *Appl. Biochem. Biotechnol.* 1994, 45-46, 87.), wool and silk (Masri, S. M., et al. *W. Polym. Prepr., Am. Chem. Soc., Div. Polym. Chem.* 1975, 16, 70), and the roots of various plants, including sunflowers, terrestrial turf grasses, and members of the family Brassicaceae. (Raskin, I. et al. PCT Int. Appl. WO94/29226 A1; *Chem. Abstr.* 1995, 122, 169223.)

Despite the techniques listed above, there nevertheless exists a need for efficient and effective processes for the removal of metals from various liquid media. Moreover, there is a particular need for processes that are capable of removing palladium from liquids that contain drug substances.

SUMMARY OF THE INVENTION

The present invention provides a process for removing a metal from a metal-containing liquid mixture. In carrying out the process of the invention, the liquid mixture is contacted with a solid extractant having a metal-binding functionality. The metal-binding functionality comprises a phosphine group, or a substituted phosphine group, which is connected to the solid extractant directly or via a linking moiety. The linking moiety does not include at least one of a hydrocarbylsilyl residue or a polyamine residue.

In a preferred embodiment, the liquid also contains another substance. In another preferred embodiment, the substance is a drug substance, or a salt, solvate, prodrug ester, stereoisomer, precursor or intermediate of a drug substance.

In another embodiment, the invention provides a method of recovering a drug substance from a liquid medium containing the drug substance together with at least one metal. The liquid medium is contacted with a solid extractant, and the drug substance is separated from the liquid medium. The solid extractant may also be separated from the liquid medium. The solid extractant has a metal-binding functionality which comprises an unsubstituted or substituted phosphine group. The metal-binding functionality is connected to the solid extractant directly or through a linking moiety. The linking moiety does not include at least one of a hydrocarbylsilyl residue or a polyamine residue.

The processes of the invention are used to advantage in the production of compounds of formula I

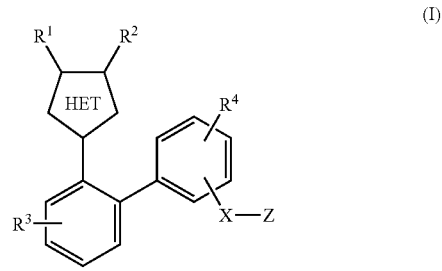

In compounds of formula I, $R^1$ and $R^2$ represent groups that are the same or different and are independently selected from hydrogen, alkyl, cycloalkyl, aryl, heterocyclo, and aralkyl.

The $R^3$ group represents hydrogen, halogen, alkyl, alkenyl, alkynyl, heterocyclo, cycloalkyl, alkylcarbonyl, polyhaloalkyl, cyano, nitro, hydroxy, amino, alkanoyl, alkylthio, alkylsulfonyl, alkoxycarbonyl, alkylaminocarbonyl, alkylcarbonylamino, alkylcarbonyloxy, or alkylaminosulfonyl.

The variable $R^4$ represents a group selected from hydrogen, halogen, alkyl, alkenyl, alkynyl, alkoxy, aryl, heterocyclo, aralkyl, arylalkenyl, arylalkynyl, cycloalkyl, alkylcarbonyl, arylcarbonyl, polyhaloalkyl, cyano, nitro, hydroxy, amino, alkanoyl, aroyl, alkylthio, alkylsulfonyl, arylsulfonyl, alkoxycarbonyl, aryloxycarbonyl, alkylaminocarbonyl, arylaminocarbonyl, alkylcarbonylamino, alkylcarbonyloxy, alkylaminosulfonyl, or arylaminosulfonyl.

If chemically capable of substitution, the $R^1$, $R^2$, $R^3$ and $R^4$ groups may optionally be substituted with up to 5 substituents selected from: hydrogen, halo, alkyl, polyhaloalkyl, alkoxy, polyhaloalkoxy, alkenyl, alkynyl, cycloalkyl, aryl, heterocyclo, aralkyl, arylalkenyl, arylalkynyl, aryloxy, arylazo, hydroxy, nitro, cyano, amino, substituted amino, thiol, alkylthio, arylthio, heterocyclothio, alkylcarbonyl, arylcarbonyl, acyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfinylalkyl, arylsulfonyl, alkylsulfonyl, aminosulfinyl, aminosulfonyl, arylsulfonylamino, heterocyclocarbonylamino, heterocyclosulfinyl, heterocyclosulfonyl, alkylsulfinyl, sulfonamido and sulfonyl.

In compounds of formula I, X represents a valence bond or a divalent linking moiety selected from $(CH_2)_n$, $O(CH_2)_n$, $S(CH_2)_n$, cycloalkylene, $N(R^5)(CH_2)_n$, $NHC(O)$, or ethenyl, where n is an integer from 0 to 5, inclusive, and $R^5$ is hydrogen, alkyl, or alkanoyl. The X group can be read from left to right or vice versa.

The Z group represents COOR or a tetrazole of the formula

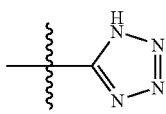

or its tautomer. The group R represents a radical selected from among H, alkyl, aryl, aralkyl, cycloalkyl, heterocyclo, alkenyl, and alkynyl.

Finally, the group

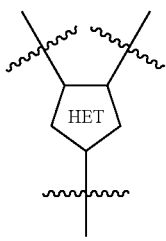

represents a heterocyclo group which may optionally be substituted at one or both of its 2 and 5 positions with one or two substituents which are independently selected from the group consisting of alkyl, alkenyl, oxo, carboxyalkyl, carboxy, cycloalkyl, alkoxy, formyl, alkanoyl, and alkoxycarbonyl.

The process is also used to advantage in the production of the salts, solvates, stereoisomers, precursors, intermediates, and prodrug esters of compounds of formula I.

In another embodiment, the invention provides a method of recovering a drug substance comprising 2'-(5-ethyl-3,4-diphenyl-1H-pyrazol-1-yl)-[1,1']-biphenyl-3-yl-oxyacetic acid, below, or its precursors, intermediates, salts, solvates, prodrug esters, and stereisomers from a liquid medium containing the drug substance together with at least one metal.

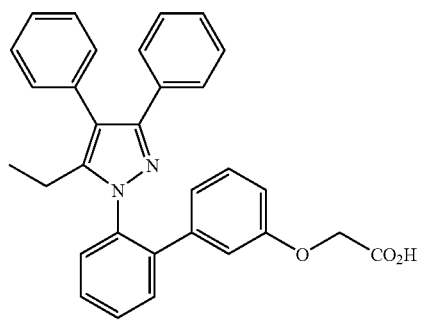

In this embodiment, the liquid medium is contacted with a solid extractant, and the drug substance is separated from the liquid medium. The solid extractant may also be separated from the liquid medium. The solid extractant has a metal-binding functionality which comprises an unsubstituted or substituted phosphine group. The metal-binding functionality is connected to the solid extractant directly or through a linking moiety. The linking moiety does not include at least one of a hydrocarbylsilyl residue or a polyamine residue.

DETAILED DESCRIPTION OF THE INVENTION

Solid extractants which are useful in the present invention include any material that is insoluble in the liquid from which the metal is to be removed and is effective to connect to a metal-binding functionality. Preferably, the solid is particulate and the size of the solid particles will be suitable for removal from the liquid by filtration. A solid having a reticulated or sponge-type morphology may also be useful in the processes of the invention.

Examples of suitable solids include carbon, inorganic polymers, calcium carbonate, alumina, silica, zeolites, clays, and organic polymers such as polystyrene, polypropylene, polyethylene, polyacrylamides, polyethylene glycol, poly(alpha-methacrylate), polybutadiene, polyamide, and the like. Preferred solids include organic polymers, and polystyrene is particularly preferred.

The metal-binding functionality may comprise any chemical moiety that is capable of forming a chemical or physical association with a metal. Examples of metal-binding functionalities include ions, electron donors, electron acceptors, ligands, chelators, and cage structures, such as zeolites. Preferably, the metal-binding functionality comprises a neutral, non-chelating electron donor. Metal-binding functionalities comprising an unsubstituted or substituted phosphine group are particularly preferred. Such substituted phosphine groups may be primary, secondary, or tertiary phosphines.

When the metal-binding functionality includes an unsubstituted or substituted phosphine, preferably the solid extractant comprises 0.1 to 10 mmol of the phosphine moiety per gram of solid, and more preferably 0.5 to 5 mmol P/g.

The metal-binding functionality is connected to the solid by chemical or physical interaction, or optionally by means of a linking moiety, which may also be connected to the solid and to the metal binding functionality by chemical or physical interaction. The connectivity is adequate if the metal remains with the solid extractant when the solid and the liquid are separated. Accordingly, preferred solids suitable for use in the invention include those having the structure:

(solid)-(linking moiety)-(metal binding functionality)

Preferred linking moieties of the invention are divalent organic groups such as arylene groups, alkylene groups, aralkylene groups, and the like. Such linking groups may optionally include one or more heteroatoms, but, if the linking moiety includes a hydrocarbylsilyl residue, then it may not also include a polyamine residue, and vice versa.

More preferred solids for use in the present invention include those having the structure:

(polymer resin)-(linking moiety)-(PL$^1$L$^2$)

wherein L$^1$ and L$^2$ are each independently chosen from among hydrogen, methyl, ethyl, propyl, isopropyl, butyl, t-butyl, cyclopentyl, substituted-cyclopentyl, cycohexyl, substituted-cyclohexyl, phenyl, substituted-phenyl, naphthyl, substituted-naphthyl, and the like. The choice of groups for L$^1$ and L$^2$ may be limited by the size of these groups, which preferably does not interfere with the interaction between the phosphorus atom and the metal.

More preferred solids for use in the present invention may be synthesized according Scheme I, below. In Scheme I, the solid sphere represents the bulk of the solid extractant.

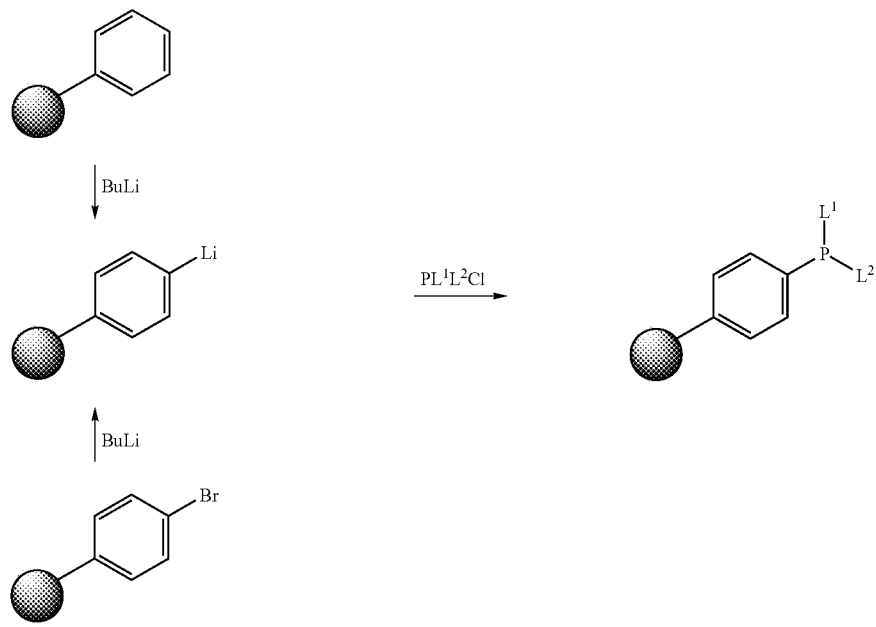

Scheme I

-continued

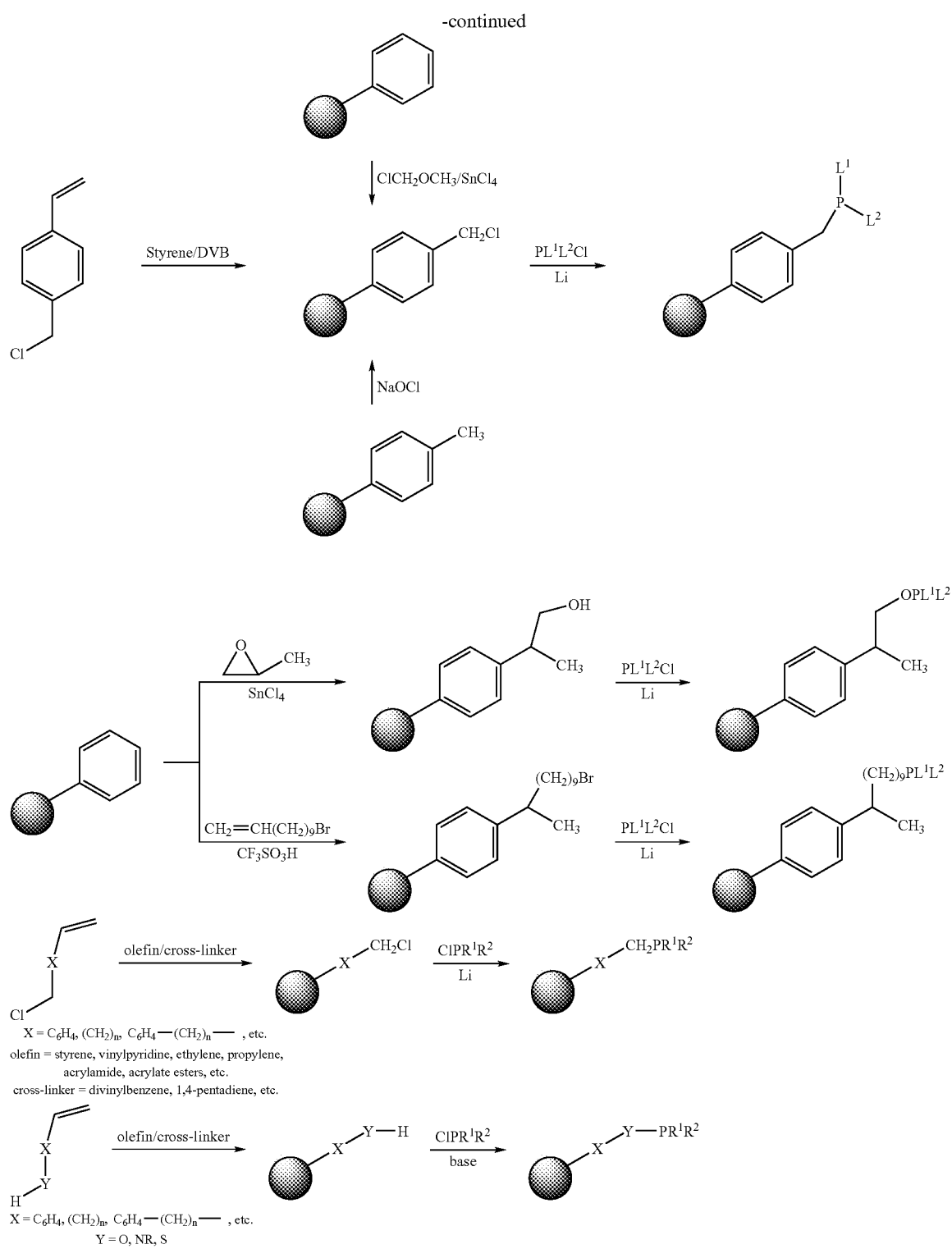

Particularly preferred solids include polystyrene comprising a triphenylphosphine moiety as the metal-binding functionality, abbreviated herein as "PS-PPh$_3$". Such solids may be synthesized by the methods depicted in the above Scheme I; alternatively, the solids may be purchased, for example, from Argonaut Technologies of Foster City, Calif., or from Fluka Chemical Corp. of Milwaukee, Wis. Preferably, the solid extractant comprises 0.1 to 3.5 mmol of PPh$_3$ per gram, and more preferably 0.5 to 3 mmol P/g.

Metals that may be removed from liquids by the methods of the present invention include alkali metals, alkaline earth metals, other main group metals, transition metals, lanthanides, and actinides.

In the present invention, a metal may be present in the liquid in the form of one or more dissolved species or solutes, in the form of one or more undissolved species, or as a mixture of dissolved and undissolved species. Examples of solutes include, e.g., manganese (II) nitrate in water. Examples of undissolved species include, e.g., colloidal particles.

Preferred metals include soft acids. Soft acids are Lewis acids having a highly polarizable acceptor center; conversely, soft bases are Lewis bases having highly polarizable donor centers. Hard and soft acid and base ("HSAB") theory was developed to account for the observation that, other variables being approximately equal, complexes of hard acids with hard bases and complexes of soft acids with soft bases are relatively more stable. See, e.g., Pearson, R. G., *J. Am. Chem. Soc.*, 1963, 85, 3533-3539; Pearson, R. G., *J. Chem. Educ.*, 1968, 45, 581; and Pearson, R. G., "Introduction to Hard and Soft Acids and Bases" (1973, Dowden, Hutchinson, Ross, Stroudsburg). Unsubstituted or substituted phosphine groups, being highly polarizable Lewis bases, can thus be classified as soft bases; according to HSAB theory, therefore, such phosphines will bind most efficiently and stably with soft acids.

Examples of soft acids include metals in the zero oxidation state, such as Ni(0), Pt(0), Pd(0), and Tl(0), and metal ions including, for example, Co(II), Ni(II), Ga(III), Pd(II), Pt(II), Pt(IV), Tl(I), Cu(I), Ag(I), Au(I), Cd(II), Hg(I), and Hg(II).

In a particularly preferred embodiment of this invention, it is contemplated that both dissolved and undissolved forms of palladium will be removed from liquids by the methods described herein.

Examples of undissolved forms of palladium include finely divided palladium, colloidal palladium, and palladium dispersed on a solid support. Examples of appropriate solid supports include carbon, inorganic polymers, calcium carbonate, alumina, silica, zeolites, clays, and organic polymers such as polystyrene, polypropylene, polyethylene, and polyamide. The palladium may be chemically bound or physically dispersed on its solid support. Palladium in its undissolved form is often employed as a heterogeneous catalyst in various organic reactions.

In the processes of the invention, the palladium is preferably in a dissolved form. Dissolved forms of palladium include its coordination complexes, assuming the liquid from which the palladium is to be removed is an appropriate solvent. Soluble palladium complexes are often employed as homogeneous catalysts in various organic reactions.

Palladium complexes are usually of the formula $Pd(0)L_n$ or $Pd(II)L_nX_2$, wherein $0 \leq n \leq 4$ and X is an anion such as $OH^-$, $Cl^-$, $Br^-$, $I^-$, triflate, mesylate, $BF_4^-$, $NO_3^-$, $^-O_2CR$ (wherein R is an alkyl or aryl group), alkyl, alkoxy, aryloxy, or an aryl anion (e.g. $Ph^-$). The palladium complexes may be dimers or oligomers of the above formula, and may also be complexed with other neutral molecules, for example, chloroform, dichloromethane, benzene, THF, heterocyclic compounds, dialkyl sulfide, dialkyl ether and the like. L represents any ligand which is appropriate for binding in a Pd complex.

Ligands L may be unidentate, bidentate, or multidentate. Examples of appropriate ligands include 1,3-dibenzylideneacetone (dba), benzonitrile (PhCN), acetonitrile ($CH_3CN$), $\eta^3$-$C_3H_5$ ($\pi$-allyl), acetylacetonate (acac). Also suitable are ligands of the formula $R'_2P(CH_2)_nPR'_2$, wherein $1 \leq n \leq 6$ and R' can be selected from hydroxy, alkyl, alkenyl, aryl, heteroaryl, alkoxy, aryloxy, amino, alkylamino, and arylamino groups. Examples of ligands of the formula $R'_2P(CH_2)_nPR'_2$, wherein R' is as previously defined, include bis(diphenylphosphino)methane (dppm); 1,2-bis(diphenylphosphino)ethane (dppe); 1,3-bis(diphenylphosphino)propane (dppp); 1,4-bis(diphenylphosphino)butane (dppb); and 1,2-bis(dimethylphosphino)ethane (dmpe)]. Also suitable are ligands of the formulae $R'_2PC\equiv CPR'_2$ [e.g. bis(diphenylphosphino)acetylene]; $R'_2PCH=CHPR'_2$ [e.g. 1,2-bis(diphenylphosphino)ethylene]; $(R'_2P)_2C=CR''R'''$ wherein R' is as previously defined and R'' and R''' are independently selected from hydrogen, halogen, alkyl, alkenyl, aryl, or heteroaryl groups [e.g. 1,1-bis(diphenylphosphino)ethylene], 1,2-bis(diphenylphosphino)benzene, 1,1'-bis(diphenylphosphino)ferrocene (dppf), 1,8-bis(diphenylphosphino)naphthalene ($DPPN_p$), 1,5-cyclooctadiene (COD), 2,2'-bipyridine (bpy), 2,2'-bis(diphenylphosphino)-1,1'-binaphthyl (BINAP). $P(R^aR^{a''}R^{a'''})$ or $As(R^aR^{a''}R^{a'''})$ are also suitable ligands. Each of $R^a$, $R^{a''}$, and $R^{a'''}$ is independently selected from hydroxy, alkyl, alkoxy, aryl, ferrocenyl, heteroaryl, aryloxy, and the like.

Other ligands suitable for complexation with palladium include:

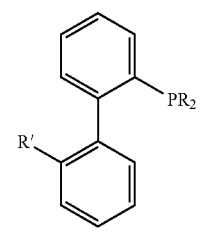

(R = Cy, tBu, 1-adamantyl;
R' = H, Me, iPr, Ph, $Me_2N$)

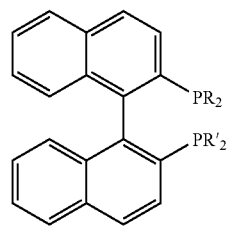

R, R' = Ph, Cy, tBu
R = R' = Ph (BINAP)

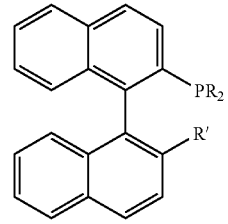

R = tBu, Ph, Me, Cy
R' = H, NMe2

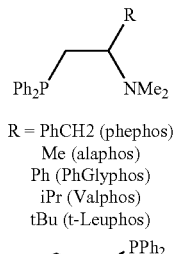

R = $PhCH_2$ (phephos)
Me (alaphos)
Ph (PhGlyphos)
iPr (Valphos)
tBu (t-Leuphos)

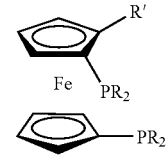

R = iPr, Ph, OPh
R = Ph, R' = Me($NMe_2$)CH (BPPFA)
R = Ph, R' = H (dppf)
R = Me, R' = H (dmpf)

R' = H ($FcPPh_2$)
Me($NMe_2$)CH (PPFA),
Me(OMe)CH (PPFOMe),
Me($PPh_2$)CH
$Me_2NCH_2$ (FcPN)
Et (PPEF)

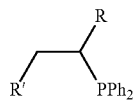

R = Me
R' = NMe2, PPh2

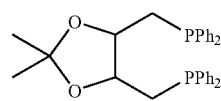

DIOP

Other appropriate ligands for palladium complexes are those which form palladacycles. Palladacycles are palladium complexes with bidentate or multidentate ligands that comprise at least one palladium-carbon bond. Examples of palladacycles include:

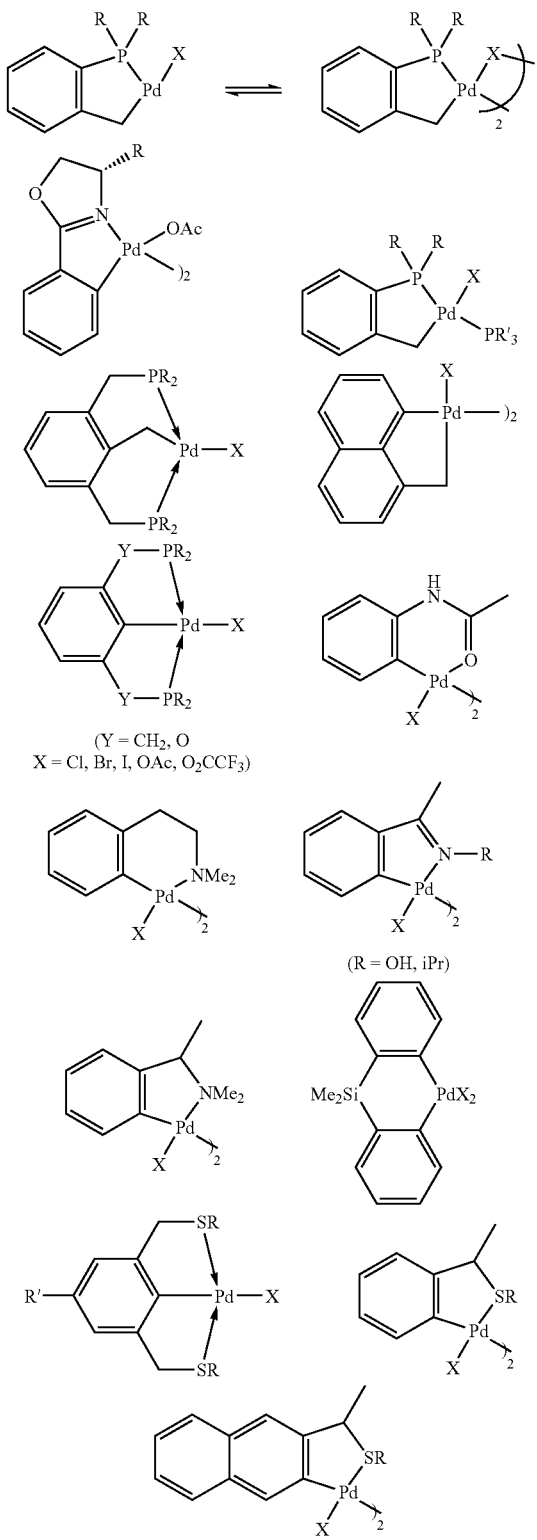

As used herein with respect to palladacycles, unless otherwise indicated in the notes accompanying the structure of a particular palladacycle, X is an anion such as OH⁻, Cl⁻, Br⁻, I⁻, triflate, mesylate, $BF_4^-$, $NO_3^-$, —$O_2CR$ (wherein R is an alkyl or aryl group), alkyl, alkoxy, aryloxy, or an aryl anion (e.g. Ph⁻), and R and R' each independently represents an alkyl or an aryl group.

Preferred ligands for palladium include dba, PhCN, $CH_3CN$, acac, $PPh_3$, dppf, dppe, dppp, dppb, and BINAP. Particularly preferred ligands for palladium include dba.

It is contemplated that the methods of the invention will be applicable to any liquid, liquid mixture, or liquid medium containing a metal. Preferred liquids, liquid mixtures, or liquid media include THF, dioxane, acetone, water, acetic acid, methanol, ethanol, isopropyl alcohol, 1-butanol, 2-methoxyethanol, dichloromethane, chloroform, acetonitrile, benzene, toluene, xylenes, mesitylene, anisole, DMF (dimethyl formamide), HMPA (hexamethylphosphoric triamide), DMSO (dimethyl sulfoxide), DMA (N,N-dimethyl acetamide), diethyl ether, methyl t-butyl ether, diisopropyl ether, 1,2-dimethoxyethane (monoglyme), 1,2-dimethoxypropane, bis(2-methoxyethyl)ether (diglyme), ethyl acetate, isopropyl acetate, ethyl propionate, ethyl vinyl ketone, butanone, hexanes, heptanes, octanes, cyclohexane, and mixtures thereof.

More preferred liquids, liquid mixtures, or liquid media include THF, alcohols (especially aliphatic alcohols), toluene, xylenes, ethers (especially alkyl ethers), acetone and other ketones, water, acetic acid, and combinations thereof. Particularly preferred liquids, liquid mixtures, or liquid media include THF, acetone, methanol, ethanol, and isopropanol, water, acetic acid, and mixtures thereof.

The methods of the present invention may be carried out at any temperature that is above the freezing point of the liquid medium and below the melting point or decomposition temperature of the solid extractant. Preferably, the liquid medium is contacted with the solid extractant at a temperature of about −20° to about 100° C. More preferably, the liquid medium is contacted with the solid extractant at a temperature of about 20° to about 60° C.

It is also contemplated that the methods of the invention will be applicable to liquids comprising one or more substances in addition to metals. The removal of the metals may, for example, constitute one step in the purification of the liquid or of the other substance(s). When the methods of the invention are used to purify another substance, the substance may be dissolved or undissolved, although preferably it is dissolved in the liquid. Also preferably, the substance being purified does not react with the metal-binding functionality.

In addition, the purification of all stereoisomers of such other substance(s) is contemplated, either in admixture or in pure or substantially pure form. Any substance whose molecules are not superimposable on their mirror images is asymmetric and therefore has at least one stereoisomer. An organic substance, for example, has an asymmetric center at any of its saturated carbon atoms to which four different moieties are bound. Consequently, substances can exist in enantiomeric or diastereomeric forms or in mixtures thereof. The processes of the invention may utilize racemates, enantiomers or mixtures of diastereomers. When diastereomeric or enantiomeric products are used or prepared, they may optionally be separated by conventional methods, for example, chromatography or fractional crystallization.

Liquids from which metals are to be removed through the methods of the invention preferably include other substances such as organic compounds, e.g., products of metal-catalyzed reactions. More preferred substances include drug substances, and the salts, stereoisomers, precursors to, and intermediates of drug substances.

Examples of drug substances include those having utility in diagnostics or imaging, as well as those capable of acting on a cell, organ or organism to create a change in the functioning of the cell, organ or organism, including but not limited to pharmaceutical agents. Such drug substances include a wide variety of substances that are used in diagnostics, therapy, immunization or otherwise are applied to combat human and animal disease. Such drug substances include but are not limited to analgesic agents, anti-inflamatory agents, antibacterial agents, antiviral agents, antifungal agents, antiparasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-glaucomic agents, mydriatic compounds and local anesthetics.

The drug substance-containing liquid mixtures on which the processes of the invention may be performed may include, without limitation, non-steroidal anti-inflammatories, such as indomethacin, salicylic acid acetate, ibuprofen, sulindac, piroxicam, and naproxen, antiglaucomic agents such as acetylcholine, anesthetics such as timolol or pilocarpine, neurotransmitters such as acetylcholine, anesthestics such as dibucaine, neuroleptics such as the phenothiazines (e.g., compazine, thorazine, promazine, chlorpromazine, acepromazine, aminopromazine, perazine, prochlorperazine, trifluoperazine, and thioproperazine), rauwolfia alkaloids (e.g., resperine and deserpine), thioxanthenes (e.g., chlorothixene and tiotixene), butyrophenones (e.g., haloperidol, moperone, trifluoperidol, timiperone, and droperidol), diphenylbutylpiperidines (e.g., pimozide), and benzamides (e.g., sulpiride and tiapride); tranquilizers such as glycerol derivatives (e.g., mephenesin and methocarbamol), propanediols (e.g., meprobamate), diphenylmethane derivatives (e.g., orphenadrine, benzotrapine, and hydroxyzine), and benzodiazepines (e.g., chlordiazepoxide and diazepam); hypnotics (e.g., zolpdem and butoctamide); beta-blockers (e.g., propranolol, acebutonol, metoprolol, and pindolol); antidepressants such as dibenzazerpines (e.g., imipramine), dibenzocycloheptenes (e.g., amtiriptyline), and the tetracyclics (e.g., mianserine); MAO inhibitors (e.g., phenelzine, iproniazide, and selegeline); psychostimulants such as phenylethylamine derivatives (e.g., amphetamines, dexamphetamines, fenproporex, phentermine, amfeprramone, and pemoline) and dimethylaminoethanols (e.g., clofenciclan, cyprodenate, aminorex, and mazindol); GABA-mimetics (e.g., progabide); alkaloids (e.g.,codergocrine, dihydroergocristine, and vincamine); anti-Parkinsonism agents (e.g., L-dopamine and selegeline); agents utilized in the treatment of Altzheimer's disease, cholinergics (e.g., citicoline and physostigimine); vasodilators (e.g., pentoxifyline); and cerebro active agents (e.g., pyritinol and meclofenoxate).

Representative examples of anti-neoplastic agents include, but are not limited to, paclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-actanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, and cholchicine.

Representative antibacterial agents include the aminoglycosides, such as gentamicin.

Representative antiviral compounds include rifampicin, 3'-azido-3'-deoxythymidine (AZT), and acyclovir.

Representative antifungal agents include the azoles, including fluconazole, macrolides such as amphotericin B, and candicidin.

Representative anti-parasitic compounds include the antimonials.

Suitable drug substances also include, without limitation, vinca alkaloids, such as vincristine and vinblastine, mitomycin-type antibiotics, such as mitomycin C and N-methyl mitomycin, bleomycin-type antibiotics such as bleomycin $A_2$, antifolates such as methotrexate, aminopterin, and dideaza-tetrahydrofolic acid, taxanes, anthracycline antibiotics and others.

Also suitable as drug substances are a variety of polypeptides, such as antibodies, toxins, including diphtheria toxin, peptide hormones, such as colony stimulating factor, and tumor necrosis factors, neuropeptides, growth hormone, erythropoietin, and thyroid hormone, lipoproteins, such as µ-lipoprotein, proteoglycans such as hyaluronic acid, glycoproteins such as gonadotropin hormone, immunomodulators or cytokines such as interferons or interleukins, as well as hormone receptors such as the estrogen receptor.

Drug substances also can comprise enzyme inhibiting agents such as reverse transcriptase inhibitors, protease inhibitors, angiotensin converting enzymes, 5µ-reductase, and the like. Typical of these agents are peptide and non-peptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 1996, 39: 3278), and didanosine. Such agents can be administered alone or in combination therapy; e.g., a combination therapy utilizing saquinavir, zalcitabine, and didanosine, zalcitabine, and zidovudine. See, for example, Collier et al., *Antiviral Res.* 1996, 29: 99.

The drug substances can also comprise nucleotides, such as thymine, nucleic acids, such as DNA or RNA, or synthetic oligonucleotides, which may be derivatized by covalently modifying the 5' or the 3' end of the polynucleic acid molecule with hydrophobic substituents to facilitate entry into cells (see for example, Kabanov et al., *FEBS Lett.* 1990, 259, 327; Kabanov and Alakhov, *J. Contr. Rel.* 1990, 28: 15). Additionally, the phosphate backbone of the polynucleotides may be modified to remove the negative charge (see, for example, Agris et al., *Biochemistry* 1968, 25:6268, Cazenave and Helene in *Antisense Nucleic Acids and Proteins: Fundamentals and Applications*, Mol and Van der Krol, Eds., p. 47 et seq., Marcel Dekker, New York, 1991), or the purine or pyrimidine bases may be modified, for example, to incorporate photo-induced crosslinking groups, alkylating groups, organometallic groups, intercalating groups, biotin, flourescent and radioactive groups (see, for example, *Antisense Nucleic Acids and Proteins: Fundamentals and Applications*, Mol and Van der Krol, Eds., p.47 et seq. Marcel Dekker, New York, 1991; Milligan et al., *In Gene Therapy for Neoplastic Diseases*, Huber and Laso, Eds. P. 228 et seq., New York Academy of Sciences, New York, 1994). Such nucleic acid molecules can be among other things antisense nucleic acid molecules, phosphodiester, oligonucleotide α-anomers, ethylphosphotriester analogs, phosphorothioates, phosphorodithioates, phosphoroethyltriesters, methylphosphonates, and the like (see, e.g., Crooke, *Anti-Cancer Drug Design* 1991, 6: 609; De Mesmaeker et al. *Acc. Chem. Res.* 1995, 28: 366). Drug substances suitable for use in the invention may also include antigene, ribozyme and aptamer nucleic acid drugs (see, for example, Stull and Szoke, *Pharm. Res.* 1995, 12: 465).

Included among the suitable drug substances are viral genomes and viruses (including the lipid and protein coat). Thus, removal of metals from a variety of viral vectors, including complete viruses of their parts, for use in gene delivery (e.g. retroviruses, adenoviruses, herpes-virus, Pox-virus) is contemplated to be within the scope of this invention. See, for example, Hodgsen, *Biotechnology*, 1995, 13, 222.

The drug substances may further include a targeting group including but not limited to antibody, fragment of an antibody, protein ligand, polysaccharide, polynucleotide, polypeptide, low molecular mass organic molecule and the like. Such targeting group can be linked covalently to a drug substance, or can be non-covalently incorporated in a drug substance through hydrophobic interactions, electrostatic interactions or hydrogen bonds.

The drug substances may be present as salts, in particular pharmaceutically acceptable salts. Drug substances having, for example, at least one basic center can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4) alkyl or arylsulfonic acids which are unsubstituted or substituted, for example by halogen, for example methanesulfonic acid or p-toluenesulfonic acid. Corresponding acid addition salts can also be formed having, if desired, an additional basic center.

Drug substances having at least one acid group (for example C(O)OH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, piperazine, pyrrolidine, a mono-, di-, or tri-lower alkylamine, for example ethyl, t-butyl, diethyl, diisopropyl, triethyl, tributyl or dimethyl-propylamine, or a mono, di, or trihydroxy lower alkylamine, for example mono, di or triethanolamine.

Corresponding internal salts may furthermore be formed. Salts which are unsuitable for pharmaceutical uses but which can be employed, for example, for the isolation or purification of free molecules of drug substances or their pharmaceutically acceptable salts, are also included within the scope of this invention.

Preferred salts of drug substances that include a basic group include monohydrochloride, hydrogen sulfate, methanesulfonate, phosphate or nitrate.

Preferred salts of drug substances that include an acid group include sodium, potassium and magnesium salts and pharmaceutically acceptable organic amines.

The process for removing metals from liquid mixtures is used to advantage in the recovery of compounds of formula I, below, and its salts, solvates, stereoisomers, precursors, intermediates, and prodrug esters from organic solvents containing spent palladium catalyst. Compounds of formula I find utility as aP2 inhibitors, for example.

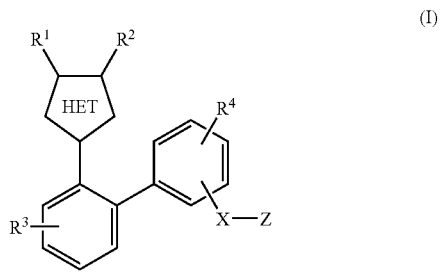

In formula I, $R^1$, $R^2$, $R^3$, $R^4$, X, Z, and

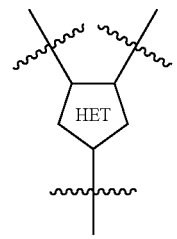

are as defined above in the Summary of the Invention.

Unless otherwise indicated, the term "alkyl", or "alk" as employed herein, alone or in combined form, e.g., haloalkyl or aralkyl, includes both straight and branched chain hydrocarbons containing 1 to 20 carbons, preferably 1 to 10 carbons, more preferably 1 to 8 carbons, in the normal chain. Examples of alkyl groups include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Each alkyl group may optionally be substituted with 1 to 4 substituents which may include halo, $CF_3$, alkoxy, aryl, aryloxy, aralkyl, aralkyloxy, alkenyl, cycloalkyl, amino, substituted amino, hydroxy, acyl, heterocyclo, heterocyclooxy, heterocycloalkoxy, aryloxyaryl, alkylamido, alkanoylamino, arylcarbonylamino, nitro, cyano, thiol, and/or alkylthio and/or any of the $R^3$ groups or substituents for $R^3$ as defined above.

The term "cycloalkyl" as employed herein, alone or in combined form, includes saturated or unsaturated cyclic hydrocarbon groups containing 1 to 3 rings, that is, monocyclic alkyl, bicyclic alkyl and tricyclic alkyl. Cycloalkyl groups may contain a total of 3 to 20 carbons forming the ring(s), preferably 3 to 10 carbons forming the ring(s), and may optionally be fused to 1 or 2 aromatic rings as described for aryl, below. Unsaturated cycloalkyl groups may contain one or two double bonds, or one triple bond. Cycloalkyl groups include cyclopropyl, cyclobutyl, cyclopentyl, cyclohexyl, cycloheptyl, cyclooctyl, cyclodecyl and cyclododecyl, cyclopentenyl, cyclohexenyl, cycloheptenyl, cyclooctenyl, cyclohexadienyl, cycloheptadienyl, and the following:

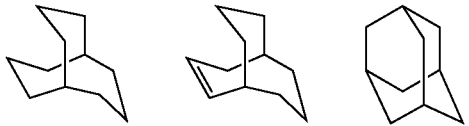

Each cycloalkyl group may be optionally substituted with 1 to 4 substituents such as halogen, alkyl, alkoxy, hydroxy, aryl, aryloxy, aralkyl, cycloalkyl, alkylamido, alkanoylamino, oxo, acyl, arylcarbonylamino, amino, substituted amino, nitro, cyano, thiol and/or alkylthio, and/or any of the $R^4$ groups or substituents for $R^4$, above.

The term "cycloalkylene" as employed herein, alone or in combined form, refers to a cycloalkyl group which includes at least two free bonds and, thus, is a linking group. Examples of cycloalkylene groups include the following:

and the like. Cycloalkylene groups may optionally be substituted with any of the substituents defined above for "cycloalkyl" groups.

The term "alkanoyl" as used herein, alone or in combined form, refers to an alkyl group linked to a carbonyl group. Alkanoyl groups may be substituted with any of the alkyl substituents listed above.

The term "alkenyl" as employed herein, alone or in combined form, refers to straight or branched chain radicals of 2 to 20 carbons, preferably 2 to 12 carbons, and more preferably 1 to 8 carbons in the normal chain, and including 1 to 6 double bonds in the normal chain. Examples of alkenyl groups include vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Alkenyl groups may be optionally substituted with 1 to 4 substituents, for example halogen, haloalkyl, alkyl, alkoxy, alkenyl, alkynyl, aryl, aralkyl, cycloalkyl, amino, substituted amino, hydroxy, heterocyclo, alkanoylamino, alkylamido, arylcarbonylamino, nitro, cyano, thiol, alkylthio, or any of the $R^3$ groups or the $R^3$ substituents set forth hereinabove.

The term "alkynyl" as employed herein, alone or in combined form, refers to straight or branched chain radicals of 2 to 20 carbons, preferably 2 to 12 carbons and more preferably 2 to 8 carbons in the normal chain, including one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Alkynyl groups may optionally be substituted with 1 to 4 substituents, for example halogen, alkyl, alkoxy, alkenyl, alkynyl, aryl, aralkyl, cycloalkyl, amino, substituted amino, heterocyclo, hydroxy, alkanoylamino, alkylamido, arylcarbonylamino, nitro, cyano, thiol, or alkylthio, or any of the $R^3$ groups or the $R^3$ substituents set forth hereinabove.

The terms "aralkenyl" and "aralkynyl" as employed herein, alone or in combined form, refers to alkenyl and alkynyl groups, as described above, having an aryl substituent.

Where alkyl groups as defined above have single bonds for attachment to other groups at two different carbon atoms, they are termed "alkylene" groups and may optionally be substituted as defined above for "alkyl" groups.

Similarly, where alkenyl groups as defined above have single bonds for attachment at two different carbon atoms, they are termed "alkenylene groups", and may optionally be substituted as defined above for "alkenyl" groups. Further, where alkynyl groups as defined above have single bonds for attachment at two different carbon atoms, they are termed "alkynylene groups", and may optionally be substituted as defined above for "alkynyl" groups.

Suitable alkylene, alkenylene or alkynylene groups $(CH_2)_n$ or $(CH_2)_p$ (where p is 1 to 8, preferably 1 to 5, and n is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, substituted amino, thioalkyl, oxo, $C_3$-$C_6$ cycloalkyl, alkylcarbonylamino or alkylcarbonyloxy.

Examples of alkylene, alkenylene and alkynylene groups include the following:

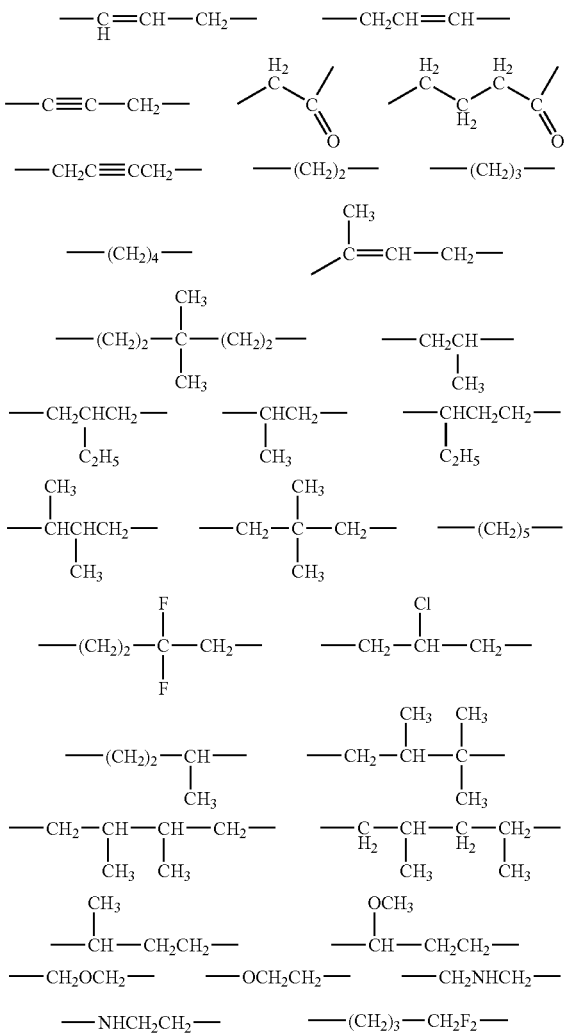

-continued

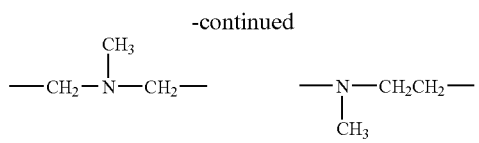

The term "halogen" or "halo" as used herein alone or in combined form refers to fluorine, chlorine, bromine, and iodine. Chlorine and fluorine are preferred.

Unless otherwise indicated, the term "aryl" as employed herein alone or in combined form, e.g., aralkyl, refers to monocyclic and bicyclic aromatic groups containing 6 to 10 carbons in the ring portion. Examples of aryl groups include phenyl or naphthyl, such as 1-naphthyl and 2-naphthyl, or indenyl. Aryl groups may optionally include one to three additional rings fused to a cycloalkyl ring or a heterocyclic ring. Further examples of aryl groups thus include the following:

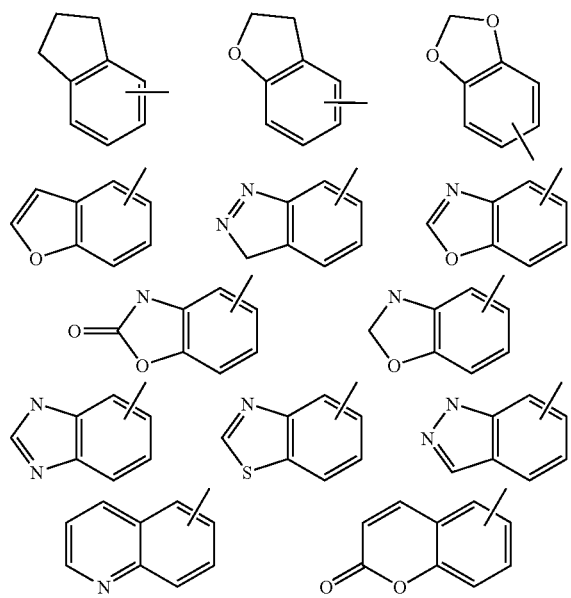

Aryl groups may be optionally substituted through available carbon atoms with 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino.

The term "aralkyl" as used herein refers to an aryl group, as defined above, bonded directly through an alkyl moiety, such as a benzyl group, for example. An aralkyl group may be optionally substituted with any group described herein as an aryl or alkyl substitutent.

The normal carbon chain of any alkyl, alkylene, alkenyl, alkenylene, alkynyl, or alkynylene group herein may optionally be interrupted by one or more heteroatoms.

Unless otherwise indicated, the terms "alkoxy", "aryloxy" and "aralkoxy" as employed herein alone or in combined form includes any of the above alkyl, aryl, or aralkyl groups linked to an oxygen atom.

Unless otherwise indicated, the term "substituted amino" as employed herein alone or in combined form refers to an amino group substituted with one or two substituents, which may be the same or different, such as alkyl, aryl, aralkyl, heterocyclo, cycloalkyl, alkoxyalkyl, or alkylthio. These substituents may be further substituted with a carboxylic acid and/or any of the $R^4$ groups or $R^4$ substituents as set forth hereinabove for formula I. When the substituted amino group has an aryl substituent, the aryl group may include 1 or 2 substituents which are alkyl, aryl or any of the moieties defined as aryl substituents, thiol, alkylthio, arylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of the $R^4$ groups or the $R^4$ substituents as set forth hereinabove for formula I. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-aralkyl-1-piperazinyl, 4-diaralkyl-1-piperazinyl, 1-pyrrolidinyl, 1-piperidinyl, or 1-azepinyl, or the like, any of which heterocycles may optionally be substituted with one or more alkyl, alkoxy, alkylthio, halo, trifluoromethyl or hydroxy groups.

The term "lower alkylthio", "alkylthio", "arylthio" or "aralkylthio" as employed herein alone or in combined form includes any of the alkyl, aralkyl or aryl groups defined hereinabove linked to a sulfur atom.

The term "acyl" as employed herein by itself or part of another group, as defined herein, refers to an organic radical linked to a carbonyl (C=O) group. Examples of acyl groups include any of the $R^3$ groups as defined above for formula I that may be attached to a carbonyl, such as alkanoyl, alkenoyl, aroyl, aralkanoyl, heterocycloyl, cycloalkanoyl, and the like.

The terms "heterocyclo", "heterocyclic" and "heterocycle" as used herein, alone or in combined form, refer to an optionally substituted, aromatic or non-aromatic cyclic group, which, for example, is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Examples of suitable monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, triazolyl, and the like.

Examples of suitable bicyclic heterocyclic groups include indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Examples of suitable substituents for heterocyclic groups include one or more alkyl groups as described above or one or more groups described above as alkyl or aryl substituents. Also suitable are aryl groups and smaller heterocycles, such as epoxides and aziridines. Substituents on heterocyclic groups may also be halogens, oxo groups, or any of the $R^4$ groups or the $R^4$ substituents as set forth hereinabove for formula I.

The term "heteroatom" as used herein includes oxygen, sulfur and nitrogen, where the nitrogen and sulfur heteroatoms may also optionally be oxidized and the nitrogen heteroatoms may also optionally be quaternized.

Heterocyclic groups, cycloalkyl groups, and cycloalkenyl groups may optionally include linking groups as described herein, e.g., alkylene, alkenylene, cycloalkylene, alkynylene, and the like.

The term "polyhaloalkyl", as used herein alone or in combined form refers to an alkyl group which includes from 2 to 9, preferably from 2 to 5, halo substituents, such as fluorine or chlorine, preferably fluorine. Examples of polyhaloalkyl groups include $CF_3CH_2$, $CF_3$ and $CF_3CF_2CH_2$.

The term "prodrug esters" as employed herein includes ester derivatives of carboxyl groups containing therapeutic agents, which derivatives are known in the art, such as methyl ester, ethyl ester, benzyl ester and the like. Other examples include the following groups: 1-(alkanoyloxy)alkyl such as

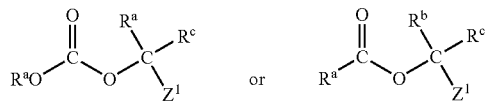

wherein $R^a$, $R^b$ and $R^c$ are H, alkyl, aryl or aralkyl; however $R^aO$ cannot be HO, and where $Z^1$ is one of the following:

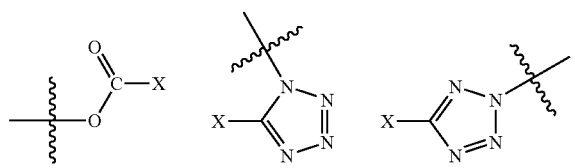

and X is as set forth hereinabove for formula I.

Examples of prodrug esters include $CH_3CO_2CH_2OC(O)$—, $CH_3CO_2CH(CH(CH_3)_2)OC(O)$—, t-$C_4H_9CO_2CH_2OC(O)$— and $C_2H_5OC(O)OCH_2OC(O)$—.

Other examples of suitable prodrug esters include the following:

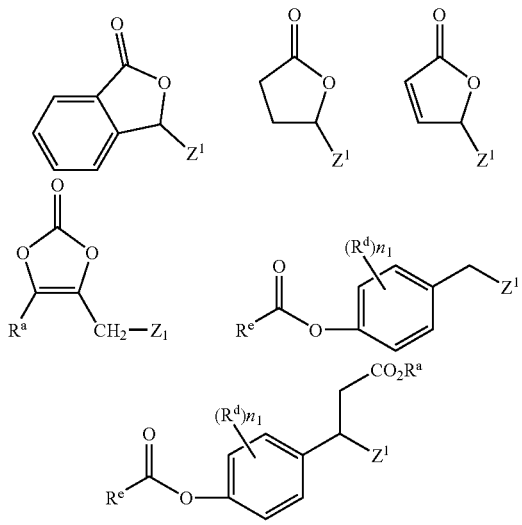

wherein $R^a$ can be H, alkyl (such as methyl or t-butyl), aralkyl (such as benzyl) or aryl (such as phenyl); $R^d$ is H, alkyl, halogen or alkoxy; $R^e$ is alkyl, aryl, aralkyl or alkoxy; $n_1$ is 0, 1 or 2; and $Z^1$ is as defined immediately above.

The term "metal" as used herein refers to an element that can exist as a positive ion in aqueous solution.

As used herein, the term "solute" refers to a dissolved substance.

The term "intermediate", as used herein, refers to a substance that is formed in the course of a chemical reaction or a series of chemical reactions and then reacts further during the conversion of reactants to products. Intermediates need not be isolated from their reaction mixtures.

The term "precursor", as used herein, refers to any substance that precedes the formation of the drug substance, for example, a starting material, a salt that is later neutralized, or a free compound that is later solvated.

As used herein, the expression "optionally substituted", as in "optionally substituted lower alkyl", "optionally substituted aryl" or the like, refers to alkyl, aryl, and other groups which may be unsubstituted or substituted with the substituents mentioned above. Further, when a moiety is described herein as optionally substituted with more than one substituent, it is intended that each of the multiple substituents be chosen independently from among the substituents mentioned above.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such.

The term "drug substance", as used herein, refers to any natural or artificially made chemical which may be used to prevent, cure, or alleviate the symptoms of a disease or other undesirable physiological condition.

The foregoing definitions apply to the terms as used throughout this specification, unless otherwise expressly limited in specific instances.

Compounds of formula I may be synthesized from intermediates of formula II as shown in the schemes set out below. See also published International Appln. No. WO00/59506. The groups $R^1$, $R^2$, $R^3$, and $R^4$, in intermediate II, are the same as described above with respect to the formula I compounds of the invention, while A is a precursor to X-Z and is described in detail in Scheme II, below, wherein $R^{10}$ is lower alkyl or benzyl.

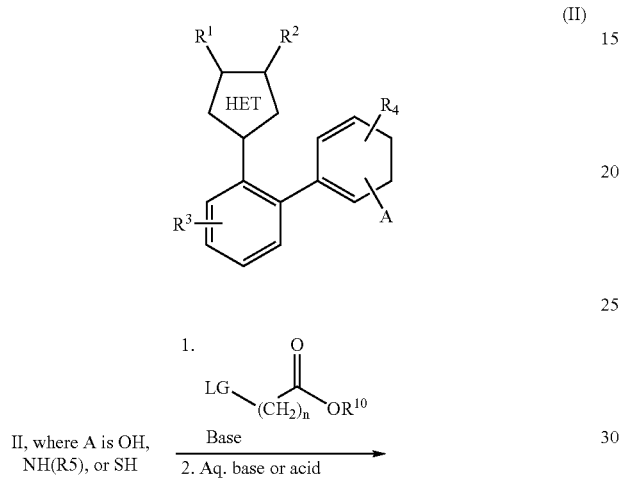
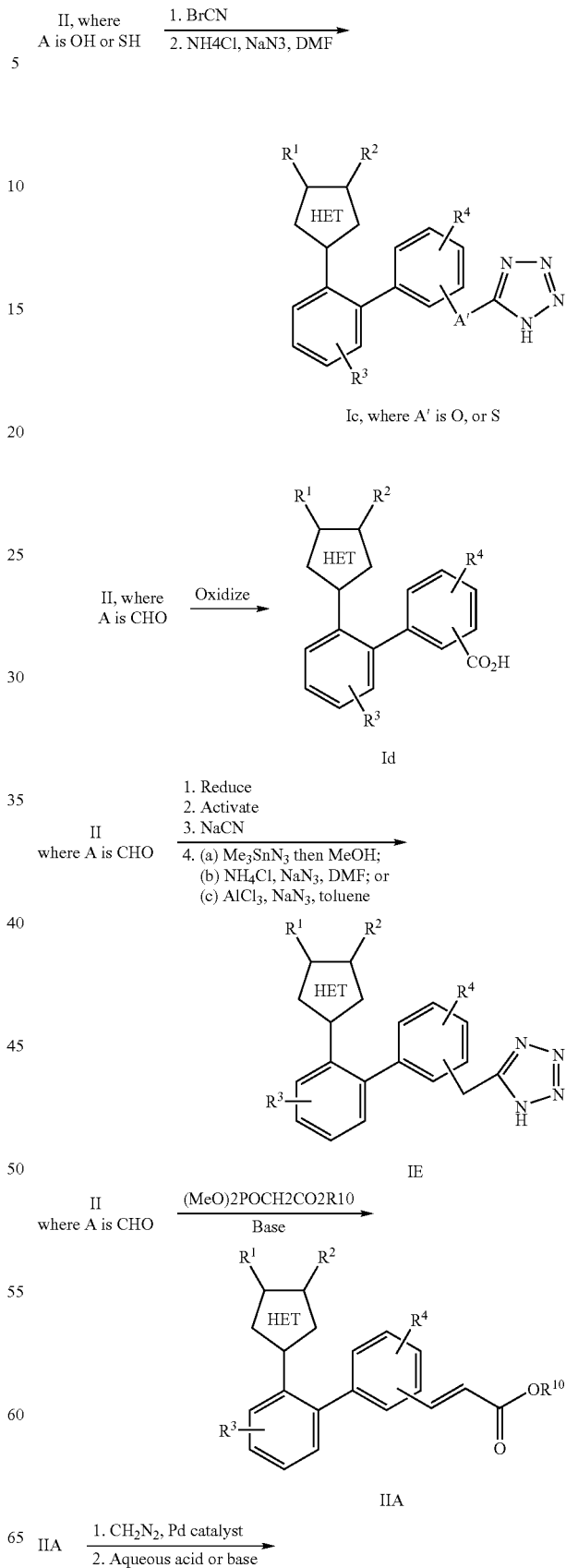

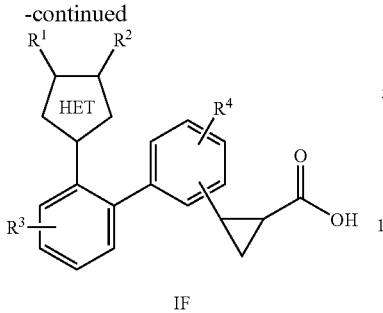

IF

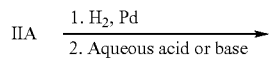

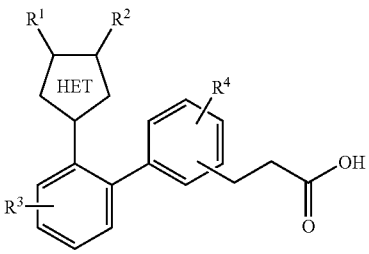

IG

The biphenyl portion of the molecule may be prepared by reaction of compound III with a substituted aryl of formula IV via Stille or Suzuki type coupling to give compounds of the formula V, as in the following reaction:

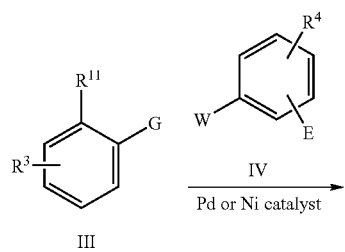

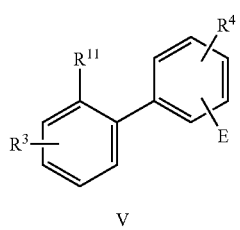

V

In compounds III, IV, and V, above, $R^4$ is as defined above, W is $B(OH)_2$, $B(OR)_2$, $SnR_3$, $ZnCl$, $ZnBr$, $ZnI$, $MgCl$, $MgBr$, $MgI$, or $SiR_3$, and G is Cl, Br, I, SR, methylsulfonate (also referred to herein as mesylate and abbreviated "OMs"), or trifluoromethanesulfonate (also referred to herein as triflate and abbreviated "OTf") or G is $B(OH)_2$, $B(OR)_2$, $SnBu_3$, or $SnR_3$ and W is Cl, Br, I, SR, OMs, or OTf. E may be CHO, CN, $CO_2R^{10}$, OH, $N(R^5)H$, $NO_2$, $SR^{10}$, $OR^{10}$, $OSi(R^{10})_3$ or preferably X-Z or a protected variant thereof, wherein R represents an alkyl group or an aryl group, and $R^{11}$ represents $CO_2R^{10}$, CHO, CN, —NH—N=C($R^2$)($CH_2R^1$), $NH_2$, or —CONH—N=CH ($R^2$), and wherein $R^1$, $R^2$, $R^3$, and $R^{10}$ are as defined previously.

Compound V, depicted below, wherein Y is

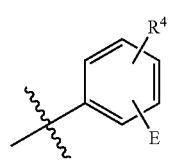

may be utilized to synthesize heterocycles of the formulae VIA-VIN by standard methods described in the literature, for example, as shown in Scheme III, below.

SCHEME III

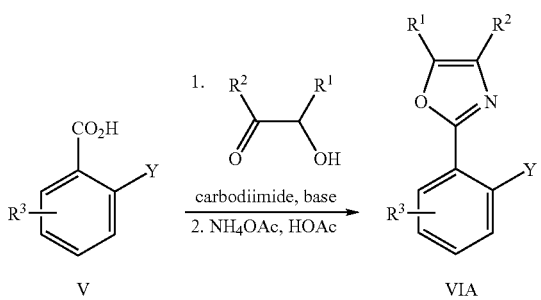

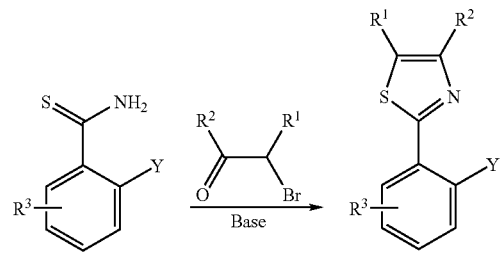

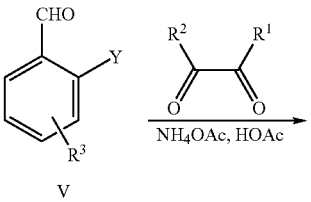

V

-continued
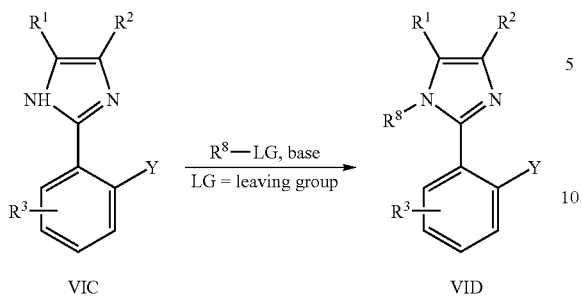
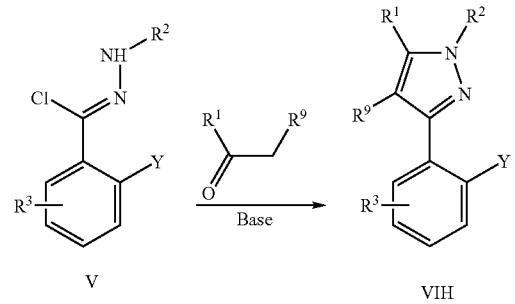
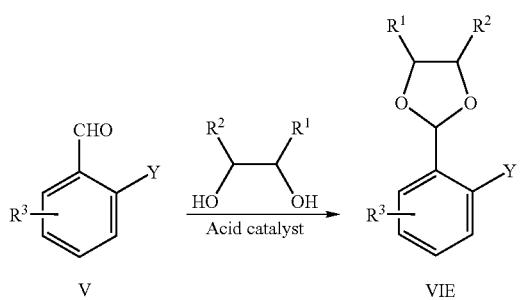
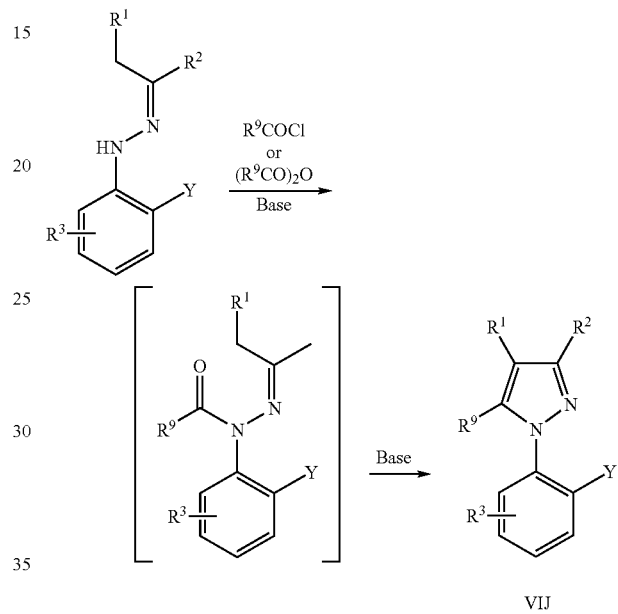
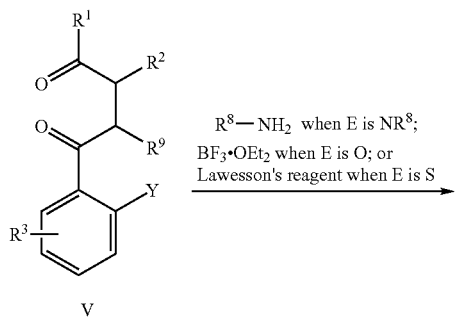
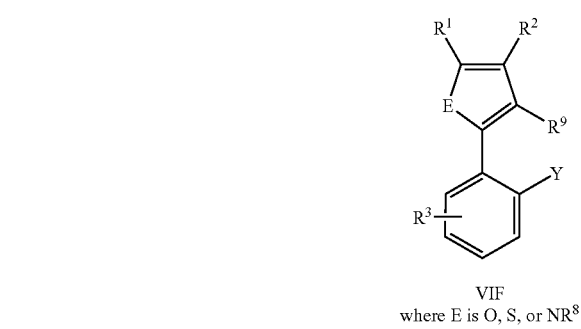
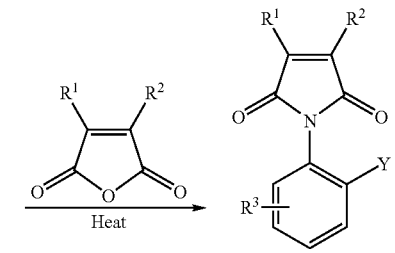
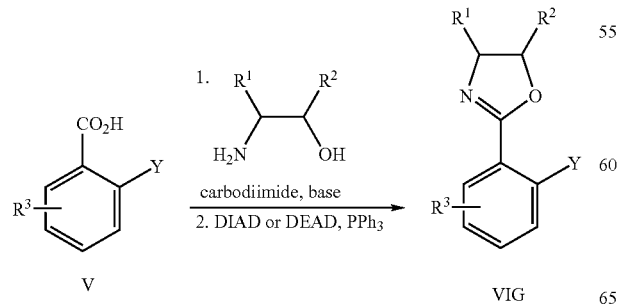
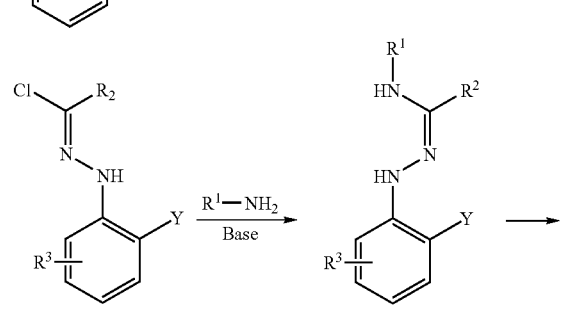

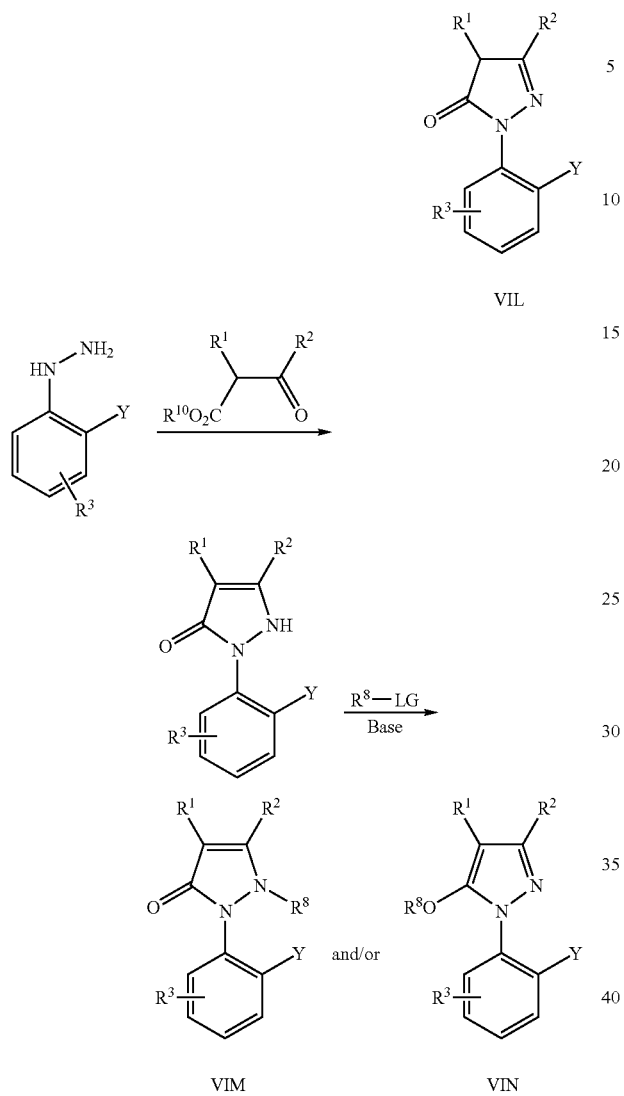

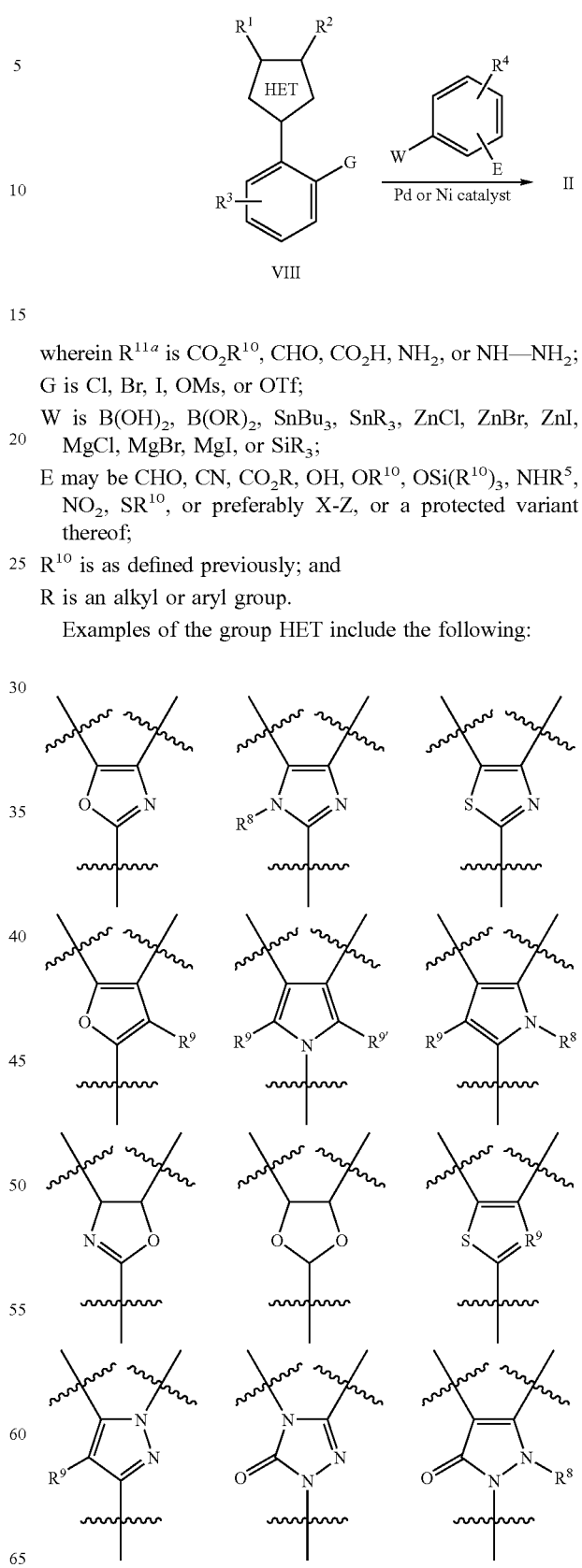

wherein $R^{11a}$ is $CO_2R^{10}$, CHO, $CO_2H$, $NH_2$, or $NH-NH_2$;

G is Cl, Br, I, OMs, or OTf;

W is $B(OH)_2$, $B(OR)_2$, $SnBu_3$, $SnR_3$, ZnCl, ZnBr, ZnI, MgCl, MgBr, MgI, or $SiR_3$;

E may be CHO, CN, $CO_2R$, OH, $OR^{10}$, $OSi(R^{10})_3$, $NHR^5$, $NO_2$, $SR^{10}$, or preferably X-Z, or a protected variant thereof;

$R^{10}$ is as defined previously; and

R is an alkyl or aryl group.

Examples of the group HET include the following:

In Scheme III, $R^1$, $R^2$, $R^3$, and Y are as defined above for formula I, $R^8$ and $R^9$ are as defined below for the HET group, $R^{10}$ is as defined above for Scheme II, and LG represents a leaving group.

Alternately, and in some cases more preferably, compounds of the formula VII may be converted to the desired heterocyclic derivatives of formula VIII by the above methodologies and subsequently converted to compounds of formula II via biphenyl coupling reactions, for example,

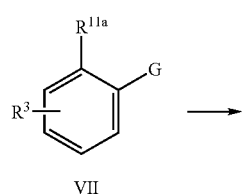

-continued

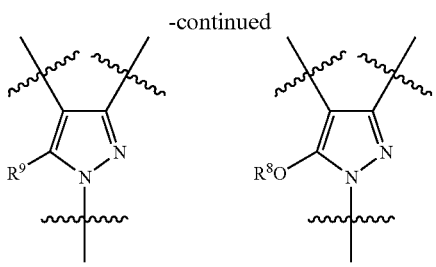

where R[8] is selected from H, alkyl, haloalkyl, hydroxyalkyl, alkoxyalkyl, or alkenyl, and R[9] and R[9] are the same or different and are selected independently from H, alkyl, alkoxy, alkenyl, formyl, $CO_2H$, $CO_2$(lower alkyl), CO(alkyl), carboxylalkyl, haloalkyl, alkenyl or cycloalkyl.

With respect to the R[8], R[9] and R[9] groups, the term "alkyl" by itself or in combined form refers to a straight or branched chain saturated hydrocarbon preferably containing 1 to 6 carbons.

Examples of X-Z moieties include (but are not limited to) the following:

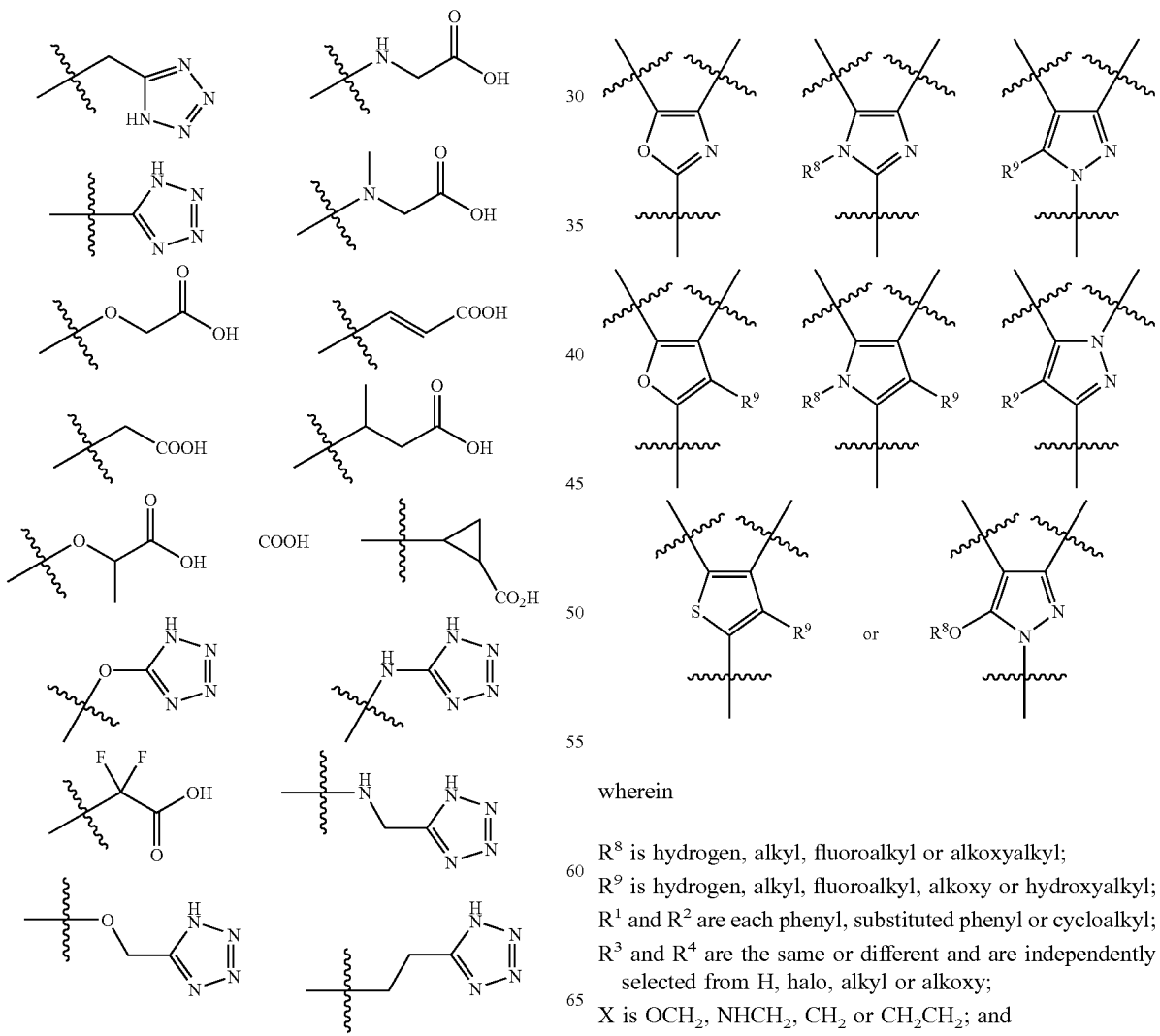

-continued

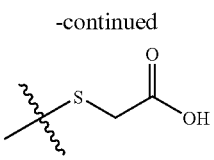

In a preferred compounds of formula I,

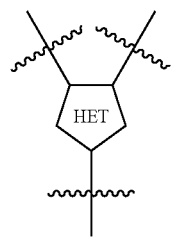

is wherein

R[8] is hydrogen, alkyl, fluoroalkyl or alkoxyalkyl;
R[9] is hydrogen, alkyl, fluoroalkyl, alkoxy or hydroxyalkyl;
R[1] and R[2] are each phenyl, substituted phenyl or cycloalkyl;
R[3] and R[4] are the same or different and are independently selected from H, halo, alkyl or alkoxy;
X is $OCH_2$, $NHCH_2$, $CH_2$ or $CH_2CH_2$; and
Z is $CO_2H$ or tetrazole.

More preferred are compounds of formula I wherein

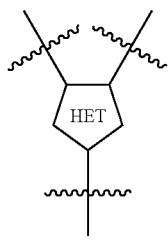

is

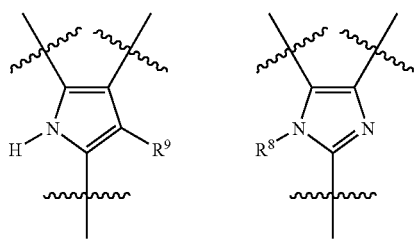

or 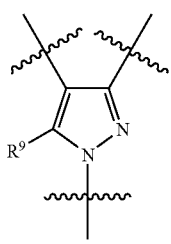

wherein $R^8$ is hydrogen, alkyl or fluoroalkyl;
$R^9$ is hydrogen, alkyl, fluoroalkyl or alkoxy;
$R^1$ and $R^2$ are each phenyl;
$R^3$ and $R^4$ are each hydrogen;
X is $OCH_2$, $CH_2$ or $NHCH_2$; and
Z is $CO_2H$ or tetrazole.

More preferred compounds of formula I include 2'-(5-ethyl-3,4-diphenyl-1H-pyrazol-1-yl)-[1,1']-biphenyl-3-yloxyacetic acid.

According to a particularly preferred embodiment of the invention, the process for removing metals from liquid mixtures is applied to the recovery of 2'-(5-ethyl-3,4-diphenyl-1H-pyrazol-1-yl)-[1,1']-biphenyl-3-yloxyacetic acid, below, or its precursors, intermediates, salts, solvates, pro-drug esters, and stereisomers from a liquid medium containing the drug substance together with at least one metal.

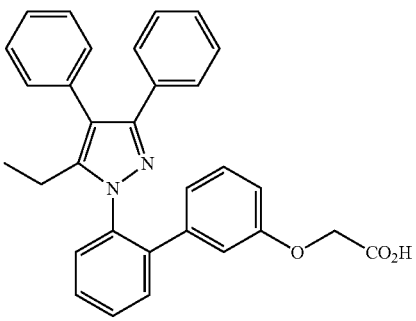

Representative examples of this preferred embodiment are provided below.

In the most efficient process currently known in the art, a liquid containing palladium and a drug substance is treated with trimercaptotriazine (TMT). The liquid usually contains solvents such as tetrahydrofuran (THF), ethanol (EtOH), methanol (MeOH), ethyl acetate, water, acetone, or their mixtures. Typical TMT treatment procedures are set forth in the examples below. The residual palladium levels of drug substances recovered after TMT treatment alone in the above solvents under neutral, acidic (HCl, HOAc, $H_2SO_4$), or basic conditions range from <10 ppm to >200 ppm.

As some drug substances, including 2'-(5-ethyl-3,4-diphenyl-1H-pyrazol-1-yl)-[1,1']-biphenyl-3-ol, a precursor of 2'-(5-ethyl-3,4-diphenyl-1H-pyrazol-1-yl)-[1,1']-biphenyl-3-yloxyacetic acid, are only sparingly soluble in acetone and other solvents, the method of palladium removal by TMT treatment suffers from several significant drawbacks, including: the necessity of handling large volumes of solvent to compensate for low solubilities, the necessity of using harsh acidic conditions (pH=1.0 to 1.5) to improve the effectiveness of palladium removal, physical loss of product in the filtration train, and poor reproducibility in the palladium levels of the final product. Furthermore, because TMT has to be removed from the mixture by crystallization of the product, the product obtained from TMT treatment is often contaminated by TMT, which affects the purity of product and causes an undesirable yellow color.

In contrast, the methods of the invention, including those employing the preferred $PS-PPh_3$ resin, can be carried out in THF, which is an excellent solvent for many drug substances, including 2'-(5-ethyl-3,4-diphenyl-1H-pyrazol-1-yl)-[1,1']-biphenyl-3-ol. The preferred methods of the invention may advantageously be carried out at room temperature.

Other advantages of the methods of the invention include: ease of handling lower volumes because of better solubility, relatively mild conditions, ease of handling, minimum loss of yield, and greater reproducibility of the palladium levels of the final product. Moreover, the final product can be isolated more readily by simply removing the solid extractant by filtration. The final product will therefore not be contaminated by residual solid extractant.

The following examples are provided to describe the invention in further detail. These examples are for illustrative purposes only, and are not intended to limit the invention in any way. All temperatures are given in centigrade degrees (° C.) unless otherwise noted.

EXAMPLE 1

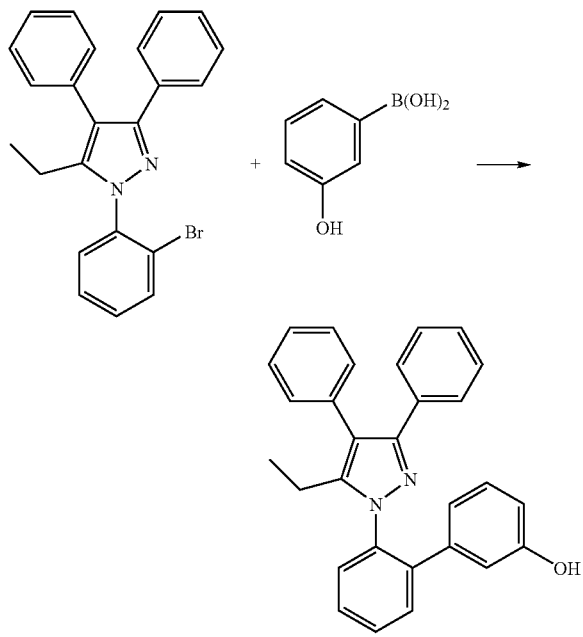

Bromophenyl pyrazole and 3-hydroxyphenylboronic acid may be purchased or synthesized according to methods described elsewhere. See, e.g., published International Appln. No. WO00/59506. Aqueous NaOH (1.5 to 2.5 equiv., about 1N to about 5N) was added to a mixture of bromophenyl pyrazole (1 equiv.), 3-hydroxyphenylboronic acid (1.05 to 1.2 equiv.), and $Pd_2(dba)_3$ (0.1 to 3.0 mole %) in ethanol (3.8 to 6.2 mL per gram of bromophenyl pyrazole). The reaction mixture was heated (55° C. to reflux temperature) under nitrogen gas with stirring for approximately 3 to 5 hours, or until the reaction was judged to be essentially complete by a high-pressure liquid chromatography (HPLC) assay. The reaction mixture was cooled to 20 to 25° C.

At this point, the reaction mixture was subjected to various procedures whose purpose was to remove the residue of the $Pd_2(dba)_3$ catalyst from the reaction product, 2'-(5-ethyl-3,4-diphenyl-1H-pyrazol-1-yl)-[1,1']-biphenyl-3-ol. Levels of residual palladium were determined by elemental analysis using inductively coupled plasma (ICP) measurements conducted with an Atomscan instrument, available from the Thermo Elemental Corporation of Franklin, Mass. All samples were dried at 50 to 55° C. under a vacuum for at least 24 h before the elemental analysis.

EXAMPLE 2

Upon completion of the cross-coupling reaction of Example 1, the reaction mixture was neutralized with HCl, and water was added to dissolve the inorganic salts and to precipitate the product, 2'-(5-ethyl-3,4-diphenyl-1H-pyrazol-1-yl)-[1,1']-biphenyl-3-ol. The precipitate of crude product was isolated by filtration. The data in Table 1, below, demonstrate that the amount of residual palladium decreases with decreasing catalyst levels.

TABLE 1

Effect of catalyst level on residual palladium.

| Concentration of $Pd_2(dba)_3$, mole % | Residual Pd, ppm |
|---|---|
| 3.0 | 1200-15000 |
| 0.5 | ~800 |
| 0.15 | 500-600 |
| 0.1 | 250-400 |

EXAMPLE 3

The reaction of Example 1 was conducted with 2 to 3 mole % of $Pd_2(dba)_3$. The reaction scale was 4.033 g (10 mmol) of bromophenyl pyrazole. After the reaction was judged to be essentially complete, 50% aqueous NaOH (about 19.1N, 1.68 equiv.) and ethanol (1.25 mL per gram of bromophenyl pyrazole starting material) were added to dissolve the precipitates, and the reaction mixture was passed twice through a Darco Zeta pad, available from Cuno, Inc. of Meridien, Conn. Trithiocyanuric acid (TMT) (0.15 equiv.) was added to the filtrate. After stirring at ambient temperature for about 3 h, the mixture was filtered three times through a new Darco pad. Neutralization of the filtrate with HCl (1N) to pH 7.0 to 7.5 afforded 2'-(5-ethyl-3,4-diphenyl-1H-pyrazol-1-yl)-[1,1']-biphenyl-3-ol as an off-white precipitate containing approximately 200 ppm of palladium.

A portion of the crude product (2 g) was redissolved in ethanol (20 mL, 10 mL/g) containing 50% NaOH (aq.) (1.5 g, 3.9 equiv.) and TMT (40 mg, 4.7 mol %). After stirring at ambient temperature for 6 h, the mixture was filtered twice through a Darco pad. Neutralization of the filtrate with 1N aq. HCl to a pH of 7.0 to 7.5 afforded 2'-(5-ethyl-3,4-diphenyl-1H-pyrazol-1-yl)-[1,1']-biphenyl-3-ol containing 19 ppm of palladium.

EXAMPLE 4

The reaction of Example 1 (reaction scale: 10 mmol of bromophenyl pyrazole) was conducted with 2.4 mole % of $Pd_2(dba)_3$. After the reaction was judged to be essentially complete, to the reaction mixture were added glacial acetic acid (7 mL/g of bromophenyl pyrazole starting material), THF (2.5 mL/g), and deionized water (7.5 mL/g). The product was only partially dissolved; therefore, more water (7.5 mL/g) was added, and the precipitates were collected by filtration. The crude product was then dissolved in a mixture of acetone (20 mL/g), acetic acid (1 mL/g), and THF (2.5 mL/g) at 50° C. TMT (0.13 equiv.) was added, and the mixture was stirred at 50° C. for about 2 h and filtered twice through a Darco pad. Neutralization of the filtrate with 1N aq. HCl to a pH of 5.3 afforded 2'-(5-ethyl-3,4-diphenyl-1H-pyrazol-1-yl)-[1,1']-biphenyl-3-ol as an off-white precipitate containing 71 ppm of palladium.

EXAMPLE 5

The reaction of Example 1 (reaction scale: 10 mmol of bromophenyl pyrazole) was conducted with 2.5 mole % of $Pd_2(dba)_3$. After the reaction was judged to be essentially complete, 50% aqueous NaOH (about 19.1N, 1.5 equiv.) was added to dissolve the organic product, and the reaction mixture was passed through a Darco zeta pad. Neutralization of the filtrate with 1N aq. HCl to a pH between 7.0 and 7.5 afforded 2'-(5-ethyl-3,4-diphenyl-1H-pyrazol-1-yl)-[1,1']-biphenyl-3-ol as an off-white solid containing 218 ppm of palladium.

The crude product was redissolved in ethanol (7.5 mL/g of bromophenyl pyrazole starting material) containing 50% aq. NaOH (2.4 equiv.) and TMT (0.23 equiv.). After stirring at ambient temperature for 18 h, additional 50% aq. NaOH (1.75 equiv.) and EtOH (2.5 mL/g) were added to dissolve the precipitates, and the resulting suspension was filtered four times through a Darco pad. Neutralization of the filtrate with 1N aq. HCl to a pH of 7.0 afforded 2'-(5-ethyl-3,4-diphenyl-1H-pyrazol-1-yl)-[1,1']-biphenyl-3-ol as a precipitate containing 23 ppm of palladium.

EXAMPLE 6

The reaction of Example 1 (reaction scale: 10 mmol of bromophenyl pyrazole) was conducted with 2.5 mole % of $Pd_2(dba)_3$. After the reaction was judged to be essentially complete, 50% aqueous NaOH (about 19.1N, 2 equiv.) was added to dissolve the organic product, and the reaction mixture was passed three times through a Darco zeta pad. Neutralization of the filtrate with 1N HCl to a pH between 7.0 and 7.5 afforded 2'-(5-ethyl-3,4-diphenyl-1H-pyrazol-1-yl)-[1,1']-biphenyl-3-ol as an off-white solid containing 199 ppm of palladium.

The crude product was dissolved in a mixture of ethanol (10 mL/g of bromophenyl pyrazole starting material) and THF (9 mL/g) containing 5N aq. HCl (1 equiv.), and TMT (0.13 equiv.). After stirring at ambient temperature for 19 h, the mixture was filtered four times through a Darco pad. Adjusting the pH of the filtrate with 1N aq. NaOH to 9.5, then neutralizing with 1N aq. HCl to a pH of 7.0 to 7.5 afforded 2'-(5-ethyl-3,4-diphenyl-1H-pyrazol-1-yl)-[1,1']-biphenyl-3-ol as a precipitate containing 6 ppm of palladium.

EXAMPLE 7

The reaction of Example 1 (reaction scale: 10 mmol of bromophenyl pyrazole) was conducted with 1 mole % of $Pd_2(dba)_3$. After the reaction was judged to be essentially complete, THF (5 mL/g of bromophenyl pyrazole starting material) was added to dissolve the precipitated crude product, and the mixture was filtered through a Darco zeta pad, which was then rinsed with THF (7.5 mL/g) and water (2.5 mL/g). The filtrate was acidified with 5N aq. HCl to a pH of 2.00, and additional THF (3.75 mL/g) was added to replace the THF lost through evaporation during vacuum filtration, and thereby re-dissolve the product.

The two phases of the resulting biphasic mixture were separated. To the organic, product-rich solution was added TMT (0.15 equiv.). The mixture was stirred at ambient temperature for 25 h and then filtered four times through a Darco zeta pad. The THF was removed by evaporation, and the resulting solid was purified by trituration with ethanol (7.5 mL/g) and DI water (3.75 mL/g) to afford 2'-(5-ethyl-3,4-diphenyl-1H-pyrazol-1-yl)-[1,1']-biphenyl-3-ol containing 342 ppm of palladium.

EXAMPLE 8

The reaction of Example 1 (reaction scale: 10 mmol of bromophenyl pyrazole) was conducted with 0.5 mole % of $Pd_2(dba)_3$. After the reaction was judged to be essentially complete, 5N aqueous HCl (1.25 mL/g of bromophenyl pyrazole starting material) was added followed by THF (12.5 mL/g) and water (2.5 mL/g). The mixture was heated to 50° C. to dissolve the precipitates, then cooled to 25° C. and filtered twice through a Darco zeta pad. To the filtrate was added TMT (5 mol %). The mixture was stirred at ambient temperature for 14 h and filtered again four times through the same Darco zeta pad employed in the previous filtration. The THF was removed by evaporation, and water (2.5 mL/g) and ethanol (2.5 mL/g) were added to precipitate the product, affording 2'-(5-ethyl-3,4-diphenyl-1H-pyrazol-1-yl)-[1,1']-biphenyl-3-ol containing 146 ppm of palladium.

EXAMPLE 9

The reaction of Example 1 (reaction scale: 10 mmol of bromophenyl pyrazole) was conducted with 0.5 mole % of $Pd_2(dba)_3$. After the reaction was judged to be essentially complete, THF (5 mL/g of bromophenyl pyrazole starting material) and 5M aqueous $H_2SO_4$ (3.75 equiv.) were added. The mixture was heated to 55° C. to dissolve the precipitates, then cooled to about 30° C. and filtered through a Darco zeta pad. The solvents were removed by evaporation, and water (7.5 mL/g) was added to the crude reaction product. Neutralization of the resulting suspension with 1N aqueous NaOH to a pH of 7.0 to 7.5 followed by filtration afforded 2'-(5-ethyl-3,4-diphenyl-1H-pyrazol-1-yl)-[1,1']-biphenyl-3-ol as a solid containing 457 ppm of palladium.

The crude product was redissolved in a mixture of ethanol (2.5 mL/g starting material) and THF (7.5 mL/g) containing $H_2SO_4$ (5M aq., 0.5 equiv.). TMT (3 mol %) was added. After stirring at ambient temperature for 20 h, the mixture was filtered four times through a Darco zeta pad. The filtrate was evaporated to dryness to afford 2'-(5-ethyl-3,4-diphenyl-1H-pyrazol-1-yl)-[1,1']-biphenyl-3-ol as a solid containing 77 ppm of palladium. Water (7.5 mL/g) was added to this product, and the slurry was neutralized with 1N aq. NaOH to a pH of 7.55 to afford 2'-(5-ethyl-3,4-diphenyl-1H-pyrazol-1-yl)-[1,1']-biphenyl-3-ol containing 79 ppm of palladium.

EXAMPLE 10

The reaction of Example 1 (reaction scale: 10 mmol of bromophenyl pyrazole) was conducted with 0.1 mole % of $Pd_2(dba)_3$. After the reaction was judged to be essentially complete, the reaction mixture was neutralized with 1N aqueous HCl to a pH of 7.0 to 7.5. The crude product, whose palladium level was 270 ppm, was dissolved in acetone (16 mL/g of bromophenyl pyrazole starting material) and THF (2.65 mL/g) at 50° C. TMT (0.23 equiv.) was added, and the mixture was stirred at 50° C. for 15 min, cooled to room temperature, and filtered three times through a Darco zeta pad. A sample of filtrate was evaporated to dryness, affording a solid containing 92 ppm of palladium. The remaining filtrate was concentrated and recrystallized by adding water, affording 2'-(5-ethyl-3,4-diphenyl-1H-pyrazol-1-yl)-[1,1']-biphenyl-3-ol containing 51 ppm of palladium.

EXAMPLE 11

The reaction of Example 1 (reaction scale: 10 mmol of bromophenyl pyrazole) was conducted with 0.2 mole % of $Pd_2(dba)_3$. After the reaction was judged to be essentially complete, 50% aq. NaOH (1.65 equiv) was added to dissolve the precipitates, and the mixture was filtered through a Darco zeta pad. Neutralization of the reaction mixture with 1N aq. HCl to a pH of 7.0 to 7.5 afforded the crude product as a precipitate containing 201 ppm of palladium.

The crude product was dissolved in acetone (22.5 mL/g of bromophenyl pyrazole starting material) containing TMT (0.11 equiv) at reflux temperature (58 to 60° C.). The mixture was stirred 30 min, then cooled to 28° C. within 30 min, causing the formation of some precipitates. This suspension was filtered three times through a Darco zeta pad. The precipitates which had accumulated on the filter pad were redissolved by rinsing the filtration train with additional acetone (60 mL/g of starting material). A portion of the resulting filtrate was evaporated to dryness to afford 2'-(5-ethyl-3,4-diphenyl-1H-pyrazol-1-yl)-[1,1']-biphenyl-3-ol containing 3 ppm of palladium.

The remaining filtrate was heated to reflux to dissolve the precipitates. The solution was concentrated by partial evaporation of the organic solvents and recrystallized by the addition of water to afford 2'-(5-ethyl-3,4-diphenyl-1H-pyrazol-1-yl)-[1,1']-biphenyl-3-ol containing 2 ppm of palladium.

EXAMPLE 12

The reaction of Example 1 (reaction scale: 10 mmol of bromophenyl pyrazole) was conducted with 0.2 mole % of $Pd_2(dba)_3$. When the reaction was judged to be essentially complete, the reaction mixture was neutralized with 1N aq. HCl to a pH of 7.0 to 7.5. After filtration, the crude solid was dissolved in acetone (20 mL/g of bromophenyl pyrazole starting material) at reflux temperature. TMT (0.11 equiv.) was added, and the mixture was stirred for 1 h while temperature was allowed to decrease to 30° C. The solution was filtered three times through a Darco zeta pad to yield a crude product whose palladium level was 356 ppm. The remaining filtrate was heated to reflux and concentrated by removing a portion of the organic solvents through distillation. Recrystallization from acetone/water afforded 2'-(5-ethyl-3,4-diphenyl-1H-pyrazol-1-yl)-[1,1']-biphenyl-3-ol containing 52 ppm of palladium.

EXAMPLE 13

The reaction of Example 1 (reaction scale: 10 mmol of bromophenyl pyrazole) was conducted with 0.15 mole % of $Pd_2(dba)_3$. After the reaction was judged to be essentially complete, the reaction mixture was neutralized with 1N aq. HCl to a pH of 7.0 to 7.5. After filtration, the crude solid was dissolved in acetone (20 mL/g of bromophenyl pyrazole starting material) at 50° C. TMT (0.11 equiv.) was added, and the mixture was stirred for 1.5 h while the temperature was allowed to decrease to 30° C. The solution was filtered three times through a Darco zeta pad to yield a crude product whose palladium level was 111 ppm. The remaining filtrate was heated to reflux and concentrated by removing a portion of the organic solvents through distillation. Recrystallization from acetone/water afforded 2'-(5-ethyl-3,4-diphenyl-1H-pyrazol-1-yl)-[1,1']-biphenyl-3-ol containing 42 ppm of palladium.

EXAMPLE 14

The reaction of Example 1 (reaction scale: 10 mmol of bromophenyl pyrazole) was conducted with 0.15 mole % of $Pd_2(dba)_3$. After the reaction was judged to be essentially complete, the reaction mixture was neutralized with 1N aq. HCl to a pH of 7.0 to 7.5. After filtration, the crude solid was dissolved in acetone (25 mL/g of bromophenyl pyrazole starting material) at 55° C. TMT (0.05 equiv.) was added, and the mixture was stirred for 1 h while the temperature was allowed to decrease to 30° C. The resulting solution was filtered twice through a Darco zeta pad. The filtrate was concentrated by partial removal of the organic solvents. Recrystallization from acetone/water afforded 2'-(5-ethyl-3,4-diphenyl-1H-pyrazol-1-yl)-[1,1']-biphenyl-3-ol containing 33 ppm of palladium.

EXAMPLE 15

The reaction of Example 1 (reaction scale: 10 mmol of bromophenyl pyrazole) was conducted with 0.15 mole % of $Pd_2(dba)_3$. After the reaction was judged to be essentially complete, the reaction mixture was neutralized with 1N aq. HCl to a pH of 7.0 to 7.5. After filtration, the crude solid was dissolved in acetone (30 mL/g of bromophenyl pyrazole starting material) at reflux. TMT (0.22 equiv.) was added at 55° C., and the mixture was stirred for 20 min while its temperature was allowed to decrease to 30° C. The mixture was filtered twice through a Darco zeta pad. The filtrate was concentrated by partial removal of the organic solvents and recrystallized from acetone/water to afford 2'-(5-ethyl-3,4-diphenyl-1H-pyrazol-1-yl)-[1,1']-biphenyl-3-ol containing 28 ppm of palladium.

EXAMPLE 16

Two portions of crude solid 2'-(5-ethyl-3,4-diphenyl-1H-pyrazol-1-yl)-[1,1']-biphenyl-3-ol containing 141 ppm of palladium were dissolved, the first portion in THF and the second in acetone. Each solution was stirred with 50 weight % PS-PPh$_3$ resin (Argonaut Technologies, 1.61 mmol PPh$_3$/g) at ambient temperature for approximately 64 h, then filtered through a 0.2 μm nylon Zap-Cap filter. After removal of the solvents, the palladium content of the product was 4ppm and 3ppm, for the portions dissolved in THF and acetone, respectively.

EXAMPLE 17

The reaction of Example 1 (reaction scale: 10 mmol of bromophenyl pyrazole) was conducted with 0.15 mole % of $Pd_2(dba)_3$. After the reaction was judged to be essentially complete, the reaction mixture was neutralized with 1N aq. HCl to a pH of 7.0 to 7.5. After filtration, the crude solid was dissolved in THF (7.5 mL/g of bromophenyl pyrazole starting material), and the mixture was filtered twice through a Darco zeta pad. PS-PPh$_3$ resin (Argonaut Technologies, 1.61 mmol PPh$_3$/g, 2.5 wt %) was added, and the mixture was stirred at ambient temperature for 5 h, then filtered through a 0.2 μm nylon Zap-Cap filter. An aliquot of the filtrate yielded a crude product whose palladium level was 37 ppm. The filtrate was concentrated by partial removal of organic solvents and recrystallized from THF/acetone/water to afford 2'-(5-ethyl-3,4-diphenyl-1H-pyrazol-1-yl)-[1,1']-biphenyl-3-ol containing 31 ppm of palladium.

EXAMPLE 18

The reaction of Example 1 (reaction scale: 10 mmol of bromophenyl pyrazole) was conducted with 0.15 mole % of $Pd_2(dba)_3$. After the reaction was judged to be essentially complete, THF (10 mL/g of bromophenyl pyrazole starting material) was added to dissolve the precipitates, and the solution was passed through a Darco zeta pad twice. The filtrate was neutralized with 1N aq. HCl to a pH of 7.0 to 7.5.

After filtration, the crude solid, whose palladium level was 111 ppm, was dissolved in THF (9 mL/g of bromophenyl pyrazole starting material), and the mixture was stirred in the presence of PS-PPh$_3$ resin (Argonaut Technologies, 1.61 mmol PPh3/g, 5 wt %) at ambient temperature for 21 h, then filtered twice through a Darco zeta pad. The filtrate was concentrated and the product was recrystallized from THF/acetone/water to afford 2'-(5-ethyl-3,4-diphenyl-1H-pyrazol-1-yl)-[1,1']-biphenyl-3-ol containing less than 2 ppm of palladium.

EXAMPLE 19

The reaction of Example 1 (reaction scale: 10 mmol of bromophenyl pyrazole) was conducted with 0.2 mole % of Pd$_2$(dba)$_3$. After the reaction was judged to be essentially complete, the reaction mixture was neutralized with 1N aq. HCl to a pH of 7.0 to 7.5. After filtration, the crude solid was dissolved in THF (8 mL/g of bromophenyl pyrazole starting material) at ambient temperature, and the mixture was filtered through a Darco zeta pad. An aliquot of the filtrate yielded crude product whose palladium level was 102 ppm. The filtrate was divided into six equal portions. To each portion was added a different amount of PS-PPh$_3$ resin (Argonaut Technologies, 1.61 mmol PPh$_3$/g). After stirring at ambient temperature for approximately 25 h, each portion was further divided into three portions and passed through three different filtering agents, respectively. The filtrates were evaporated to dryness and assayed for palladium levels. The results are summarized in the following table.

TABLE 2

Effect of amount of PS-PPh$_3$ resin and filtering agent on palladium level (ppm).

| | PS-PPh$_3$ (wt %) | | | | | |
|---|---|---|---|---|---|---|
| | 0.0 | 2.0 | 3.9 | 6.0 | 8.1 | 9.9 |
| 0.2 μm ZAP-CAP | 104 | 37 | 21 | 19 | 11 | 12 |
| Filter paper (#1) | 68 | 35 | 30 | 15 | 14 | 13 |
| Darco zeta pads | 26 | 14 | 7 | 5 | 4 | 6 |

EXAMPLE 20

The reaction of Example 1 (reaction scale: 50 mmol of bromophenyl pyrazole) was conducted with 0.2 mole % of Pd$_2$(dba)$_3$. After the reaction was judged to be essentially complete, the reaction mixture was neutralized with 1N aq. HCl to a pH of 7.0 to 7.5. The resulting precipitates, whose palladium level was 817 ppm, were collected by filtration and dissolved in THF (7 mL/g of bromophenyl pyrazole starting material). The solution was passed through a Darco zeta pad. An aliquot of this filtrate yielded a crude product whose palladium level was 169 ppm. The remaining filtrate was divided into five equal portions. To each portion was added a different amount of PS-PPh$_3$ resin (Fluka, 3.0 mmol PPh$_3$/g). While stirring at ambient temperature, sample aliquots were taken at various time intervals and filtered through a Darco zeta pad (R52SP). The solvents were removed, and the crude product thus obtained was assayed for palladium content. The assay results are summarized in the following table.

TABLE 3

Effect of amount of PS-PPh$_3$ resin and treatment time on palladium level.

| PS-PPh$_3$ resin (wt %) | Pd Level (ppm) (Time = 5~6 h) | Pd Level (ppm) (Time = 22~23 h) |
|---|---|---|
| 0 | 25 | 27 |
| 1.2 | 15 | 7 |
| 2.1 | 9 | 5 |
| 3.3 | 8 | 4 |
| 5.0 | 7 | 3 |

EXAMPLE 21

The reaction of Example 1 (reaction scale: 50 mmol of bromophenyl pyrazole) was conducted with 0.2 mole % of Pd$_2$(dba)$_3$. After the reaction was judged to be essentially complete, the reaction mixture was neutralized with 1N aq. HCl to a pH of 7.0 to 7.5. After filtration, the crude solid was dissolved in THF (8 mL/g of bromophenyl pyrazole starting material). The solution was passed through a Darco zeta pad twice, and the solvents were removed from a sample aliquot of the filtrate to yield a crude product whose palladium level was 498 ppm.

The remaining filtrate was stirred in the presence of PS-PPh$_3$ resin (Fluka, 3.0 wt %) at ambient temperature for 5 h and then filtered through a Darco zeta pad. Removal of solvents from an aliquot of ths filtrate yielded a crude product whose palladium level was 48 ppm. This filtrate was concentrated by partial removal of solvents. Recrystallization from THF/acetone/water afforded 2'-(5-ethyl-3,4-diphenyl-1H-pyrazol-1-yl)-[1,1']-biphenyl-3-ol containing 33 ppm of palladium.

EXAMPLE 22

The reaction of Example 1 (reaction scale: 50 mmol of bromophenyl pyrazole) was conducted with 0.15 mole % of Pd$_2$(dba)$_3$. After the reaction was judged to be essentially complete, the reaction mixture was neutralized with 1N aq. HCl to a pH of 7.0 to 7.5. After filtration, the crude solid was dissolved in THF (6.5 mL/g of bromophenyl pyrazole starting material), and the solution was passed through a Darco zeta pad three times. An aliquot of the filtrate yielded crude product whose palladium level was 387 ppm.

The filtrate was stirred in the presence of PS-PPh$_3$ resin (Fluka, 2.5 wt %) at ambient temperature for 17 h and then filtered twice through a Darco zeta pad. An aliquot of this second filtrate yielded crude product whose palladium level was 31 ppm. The second filtrate was concentrated and its solute recrystallized from THF/acetone/water to afford 2'-(5-ethyl-3,4-diphenyl-1H-pyrazol-1-yl)-[1,1']-biphenyl-3-ol containing 24 ppm of palladium.

EXAMPLE 23

The reaction of Example 1 (reaction scale: 50 mmol of bromophenyl pyrazole) was conducted with 0.1 mole % of Pd$_2$(dba)$_3$. After the reaction was judged to be essentially complete, the reaction mixture was neutralized with 1N aq. HCl to a pH of 7.0 to 7.5. After filtration, the crude solid was dissolved in THF (8.5 mL/g of bromophenyl pyrazole starting material), and the solution was passed through a Darco zeta pad four times. An aliquot of the resulting filtrate yielded a crude product whose palladium level was 95 ppm.

The filtrate was stirred in the presence of PS-PPh$_3$ resin (Fluka, 2.5 wt %) at 40° C. for approximately 4.5 h and then filtered through a Darco zeta pad after cooling to 25° C. A sample aliquot of the filtrate was evaporated to dryness to yield a solid containing 40 ppm of palladium. The filtrate was concentrated and its solute recrystallized from THF/acetone/water to afford 2'-(5-ethyl-3,4-diphenyl-1H-pyrazol-1-yl)-[1,1']-biphenyl-3-ol containing 18 ppm of palladium.

EXAMPLE 24

The reaction of Example 1 (reaction scale: 50 mmol of bromophenyl pyrazole) was conducted with 0.1 mole % of Pd$_2$(dba)$_3$. After the reaction was judged to be essentially complete, the reaction mixture was neutralized with 1N aq. HCl to a pH of 7.95. After filtration, the crude solid was dissolved in THF (8.5 mL/g of bromophenyl pyrazole starting material), and the solution was passed through a Darco zeta pad twice. An aliquot of this filtrate yielded crude product whose palladium level was 249 ppm.

The filtrate was stirred in the presence of PS-PPh$_3$ resin (Fluka, 2.5 wt %) at 36 to 37° C. for 7 h, allowed to cool to 25° C., and then filtered through a Darco zeta pad. A sample of the filtrate was evaporated to dryness, affording a solid containing 15 ppm of palladium.

EXAMPLE 25

The reaction of Example 1 (reaction scale: 50 mmol of bromophenyl pyrazole) was conducted with 0.1 mole % of Pd$_2$(dba)$_3$. After the reaction was judged to be essentially complete, the reaction mixture was neutralized with 1N aq. HCl to a pH of 7.5. After filtration, the crude solid was dissolved in THF (8.5 mL/g of bromophenyl pyrazole starting material), and the solution was passed through a Darco zeta pad twice. An aliquot of this filtrate yielded crude product whose palladium level was 122 ppm.

The filtrate was stirred in the presence of PS-PPh$_3$ resin (Fluka, 2.5 wt %) at 45° C. for 6 h, allowed to cool to 25° C., and then filtered through two Darco zeta pads. An aliquot of this second filtrate yielded crude product whose palladium level was 45 ppm. The second filtrate was concentrated, and its solute recrystallized from THF/acetone/water to afford 2'-(5-ethyl-3,4-diphenyl-1H-pyrazol-1-yl)-[1,1']-biphenyl-3-ol containing 28 ppm of palladium.

EXAMPLE 26

The reaction of Example 1 (reaction scale: 50 mmol of bromophenyl pyrazole) was conducted with 0.15 mole % of Pd$_2$(dba)$_3$. After the reaction was judged to be essentially complete, the reaction mixture was neutralized with 1N aq. HCl to a pH of 7.6. After filtration, the crude solid, whose palladium level was 610 ppm, was dissolved in THF (7 mL/g of bromophenyl pyrazole starting material). The solution was passed through five Darco zeta pads. An aliquot of this filtrate yielded crude product whose palladium level was 79 ppm.

PS-PPh$_3$ resin (Fluka, 2.5 wt %) was added to the filtrate, and the mixture was stirred at 50° C. for 6 h, allowed to cool to 25° C., and then filtered once through a Darco zeta pad. A sample of the filtrate was evaporated to dryness to give a solid containing less than 13 ppm of palladium. The filtrate was concentrated and its solute recrystallized from THF/acetone/water to afford 2'-(5-ethyl-3,4-diphenyl-1H-pyrazol-1-yl)-[1,1']-biphenyl-3-ol containing less than 10 ppm of palladium.

EXAMPLE 27

The reaction of Example 1 (reaction scale: 10 mmol of bromophenyl pyrazole) was conducted with 0.15 mole % of Pd$_2$(dba)$_3$. After the reaction was judged to be essentially complete, the reaction mixture was neutralized with 1N aq. HCl to a pH of 7.0 to 7.5. After filtration, the crude solid, whose palladium level was 520 ppm, was dissolved in THF (10 mL/g of bromophenyl pyrazole starting material), and the solution was passed through a Darco zeta pad. An aliquot of this filtrate yielded crude product whose palladium level was 220 ppm.

The filtrate was stirred in the presence of PS-PPh$_3$ resin (Fluka, 3.0 wt %) at ambient temperature for 6 h. Two filtration treatments followed. The first, filtration through Whatman filter paper, yielded crude product whose palladium level was 33 ppm. The second filtration, through a Darco zeta pad, afforded a solid containing 20 ppm of palladium. The filtrate was concentrated and recrystallized from THF/acetone/water to afford 2'-(5-ethyl-3,4-diphenyl-1H-pyrazol-1-yl)-[1,1']-biphenyl-3-ol containing <10 ppm of palladium.

EXAMPLE 28

The reaction of Example 1 (reaction scale: 70 g, 173.57 mmol of bromophenyl pyrazole) was conducted with 0.1 mole % of Pd$_2$(dba)$_3$. After the reaction was judged to be essentially complete, the reaction mixture was neutralized with 1N aq. HCl to a pH of 7.0 to 7.5. The crude solid, whose palladium level was 400 ppm, was dissolved in THF (9 mL/g of bromophenyl pyrazole starting material). This solution was passed through a Whatman #1 filter paper to yield crude product whose palladium level was 290 ppm. The filtrate was next passed through a Darco zeta pad twice. The palladium level of the crude product isolated from the filtrate after the first passing was 240 ppm, and 210 ppm after the second passing.

The filtrate was next stirred in the presence of PS-PPh$_3$ resin (Fluka, 2.5 wt %) at 21° C. for 16 h, then filtered through a Whatman #1 filter paper, to yield crude product whose palladium level was 19 ppm, and then through a Darco pad, after which the palladium level of the resulting crude product was less than 10 ppm. The remainder of this filtrate was concentrated, and its solute recrystallized from THF/acetone/water to afford 2'-(5-ethyl-3,4-diphenyl-1H-pyrazol-1-yl)-[1,1']-biphenyl-3-ol containing <10 ppm of palladium.

EXAMPLE 29

The reaction of Example 1 (reaction scale: 500 g, 1.24 mol of bromophenyl pyrazole) was conducted with 0.1 mole % of Pd$_2$(dba)$_3$. After the reaction was judged to be essentially complete, the reaction mixture was neutralized with 1N aq. HCl to a pH of 7.0 to 7.5. The crude solid, whose palladium level was 350 ppm, was dissolved in THF (9 mL/g of bromophenyl pyrazole starting material), and the solution was passed through a 1 µm polish filter. After filtration through a Darco zeta pad, the resulting crude isolate had a palladium level of 160 ppm.

The filtrate was then stirred in the presence of PS-PPh$_3$ resin (Fluka, 2.5 wt %) at 45° C. for 20 h, next filtered through a Darco pad at 45° C. The palladium level after this filtration was less than 10 ppm. The filtrate was concentrated and its solute recrystallized from THF/acetone/water to afford 2'-(5-ethyl-3,4-diphenyl-1H-pyrazol-1-yl)-[1,1']-biphenyl-3-ol containing less than 10 ppm of palladium.

EXAMPLE 30

The reaction of Example 1 (reaction scale: 56.6. kg, 140.34 mol of bromophenyl pyrazole) was conducted with 0.1 mole % of $Pd_2(dba)_3$. After the reaction was judged to be essentially complete, the reaction mixture was neutralized with 1N aq. HCl to a pH of 7.0 to 7.5. The crude solid was removed by filtration, and upon drying was found to contain 420 ppm of palladium.

A mixture of the crude solid and PS-PPh$_3$ resin (Fluka, 3.0 wt %) in THF (9 L/kg of bromophenyl pyrazole starting material) was stirred at 25 to 30° C. for approximately 72 h. The resin was removed by filtration, and the filtrate was passed sequentially through a Darco zeta pad cartridge and a 1.2 μm Cuno polish filter. The palladium level of the crude isolate after each filtration was found to be less than 10 ppm. The filtrate was concentrated and its solute recrystallized from THF/acetone/water to afford 2'-(5-ethyl-3,4-diphenyl-1H-pyrazol-1-yl)-[1,1']-biphenyl-3-ol containing less than 10 ppm of palladium.

EXAMPLE 31

The reaction of Example 1 (reaction scale: 71.5 kg, 177.29 mol of bromophenyl pyrazole) was conducted with 0.1 mole % of $Pd_2(dba)_3$. After the reaction was judged to be essentially complete, the reaction mixture was neutralized with 1N aq. HCl to a pH of 7.0 to 7.5. The crude solid was dissolved in THF (9 L/Kg of bromophenyl pyrazole starting material), and the mixture was stirred in the presence of PS-PPh$_3$ resin (Fluka, 3.0 wt %) at ambient temperature. After stirring for 84.5 h, the resin was removed by filtration, and the filtrate was passed sequentially through a Darco zeta pad cartridge, then a 1.2 μm Cuno polish filter. The palladium levels after the Darco pad filtration and after polish filtration were less than 10 ppm and less than 13 ppm, respectively. The filtrate was concentrated and its solute recrystallized from THF/acetone/water to afford 2'-(5-ethyl-3,4-diphenyl-1H-pyrazol-1-yl)-[1,1']-biphenyl-3-ol containing less than 10 ppm of palladium.

EXAMPLE 32

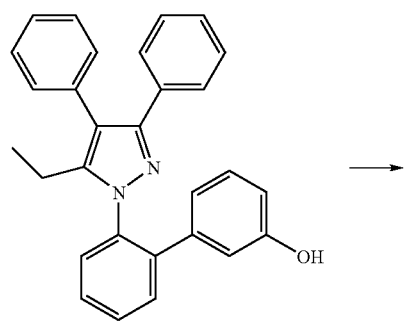

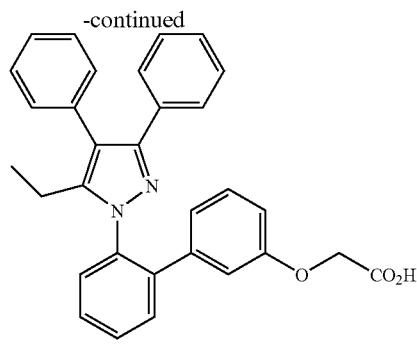

2'-(5-ethyl-3,4-diphenyl-1H-pyrazol-1-yl)-[1,1']-biphenyl-3-ol was converted to 2'-(5-ethyl-3,4-diphenyl-1H-pyrazol-1-yl)-[1,1']-biphenyl-3-yloxyacetic acid through methods that have been described elsewhere. See, e.g., published International Appln. No. WO00/59506.

A number of background publications are referenced in this application in order to more fully describe the state of the art to which this invention pertains. The entire disclosures of the publications cited above are incorporated herein by reference.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method of recovering a drug substance from a liquid medium containing said drug substance together with at least one metal, said method comprising
    contacting the liquid medium with a solid extractant having a metal-binding functionality, said metal-binding functionality comprising an unsubstituted or substituted phosphine group, said metal-binding functionality being connected to said solid extractant directly or via a linking moiety which does not include at least one of a hydrocarbylsilyl residue or a polyamine residue; and
    separating said drug substance from said liquid medium.

2. The method of claim 1, further comprising removing said solid extractant from said liquid medium.

3. A method of recovering a drug substance from a liquid medium containing said drug substance together with at least one metal, said method comprising
    contacting the liquid medium with a solid extractant having a metal-binding functionality, said metal-binding functionality comprising an unsubstituted or substituted phosphine group, said metal-binding functionality being connected to said solid extractant directly or via a linking moiety which does not include at least one of a hydrocarbylsilyl residue or a polyamine residue; and
    separating said drug substance from said liquid medium wherein said drug substance comprises a compound of formula I

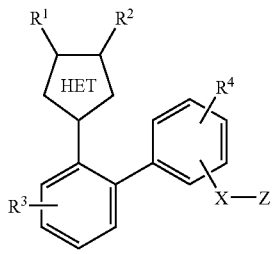

(I)

or a salt, solvate, stereoisomer, precursor, prod rug ester, or intermediate thereof, wherein

- $R^1$ and $R^2$ are the same or different and are independently selected from the group consisting of H, substituted or unsubstituted alkyl, substituted or unsubstituted cycloalkyl, substituted or unsubstituted aryl, substituted or unsubstituted heterocyclo, and substituted or unsubstituted aralkyl;
- $R^3$ is selected from the group consisting of hydrogen, halogen, substituted or unsubstituted alkyl, substituted or unsubstituted alkenyl, substituted or unsubstituted alkynyl, substituted or unsubstituted heterocyclo, substituted or unsubstituted cycloalkyl, substituted or unsubstituted alkylcarbonyl, polyhaloalkyl, cyano, nitro, hydroxy, substituted or unsubstituted amino, substituted or unsubstituted alkanoyl, substituted or unsubstituted alkylthio, substituted or unsubstituted alkylsulfonyl, substituted or unsubstituted alkoxycarbonyl, substituted or unsubstituted alkylaminocarbonyl, substituted or unsubstituted alkylcarbonylamino, substituted or unsubstituted alkylcarbonyloxy, and substituted or unsubstituted alkylaminosulfonyl;
- $R^4$ is selected from hydrogen, halogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heterocyclo, substituted or unsubstituted aralkyl, substituted or unsubstituted arylalkenyl, substituted or unsubstituted arylalkynyl, substituted or unsubstituted cycloalkyl, substituted or unsubstituted alkylcarbonyl, substituted or unsubstituted arylcarbonyl, polyhaloalkyl, cyano, nitro, hydroxy, substituted or unsubstituted amino, substituted or unsubstituted alkanoyl, substituted or unsubstituted aroyl, substituted or unsubstituted alkylthio, substituted or unsubstituted alkylsulfonyl, substituted or unsubstituted arylsulfonyl, substituted or unsubstituted alkoxycarbonyl, substituted or unsubstituted aryloxycarbonyl, substituted or unsubstituted alkylaminocarbonyl, substituted or unsubstituted arylaminocarbonyl, substituted or unsubstituted alkylcarbonylamino, substituted or unsubstituted alkylcarbonyloxy, substituted or unsubstituted alkylaminosulfonyl, and substituted or unsubstituted arylaminosulfonyl;
- $R^1$, $R^2$, $R^3$ and $R^4$ may optionally be substituted with up to 5 substituents selected from the group consisting of hydrogen, halo, alkyl, polyhaloalkyl, alkoxy, polyhaloalkoxy, alkenyl, alkynyl, cycloalkyl, aryl, heterocyclo, aralkyl, arylalkenyl, arylalkynyl, aryloxy, arylazo, hydroxy, nitro, cyano, amino, substituted amino, thiol, alkylthio, arylthio, heterocyclothio, alkylcarbonyl, arylcarbonyl, acyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfinylalkyl, arylsulfonyl, alkylsulfonyl, aminosulfinyl, aminosulfonyl, arylsulfonylamino, heterocyclocarbonylamino, heterocyclosulfinyl, heterocyclosulfonyl, alkylsulfinyl, sulfonamido and sulfonyl;
- X represents a valence bond or a divalent linking moiety which can be read from left to right or vice versa and is selected from $(CH_2)_n$, $O(CH_2)_n$, $S(CH_2)_n$, cycloalkylene, $N(R^5)(CH_2)_n$, NHCO, or ethenyl, where n is an integer from 0 to 5, inclusive, and $R^5$ is hydrogen, alkyl, or alkanoyl;
- Z is COOR or a tetrazole of the formula

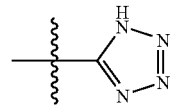

or its tautomer;
  wherein R represents a radical selected from the group consisting of H, alkyl, aryl, aralkyl, cycloalkyl, heterocyclo, alkenyl, and alkynyl; and the group

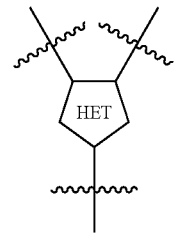

represents a heterocyclo group which may optionally be substituted with one or two substituents which are independently selected from the group consisting of alkyl, alkenyl, oxo, carboxyalkyl, carboxy, cycloalkyl, alkoxy, formyl, alkanoyl, and alkoxycarbonyl, including all stereoisomers thereof.

4. The process of claim 3, wherein, in formula I,

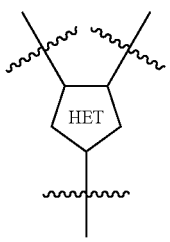

represents

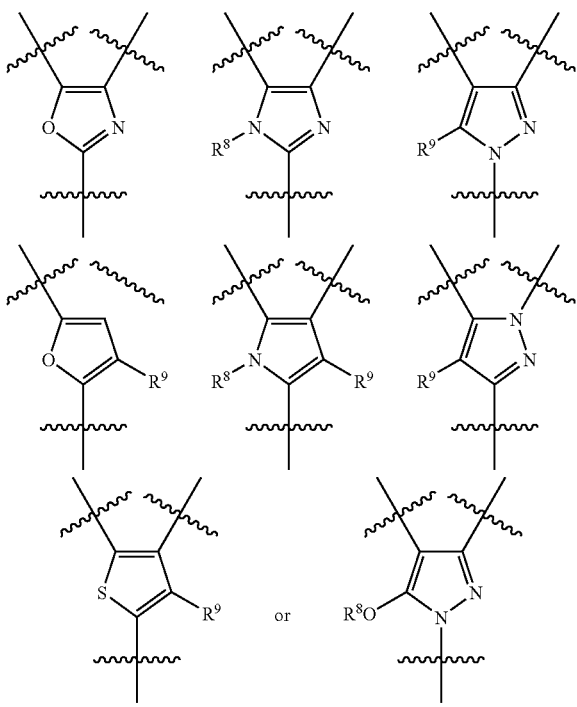

wherein
R⁸ is hydrogen, alkyl, fluoroalkyl or alkoxyalkyl; and
R⁹ is hydrogen, alkyl, fluoroalkyl, alkoxy or hydroxyalkyl;
and wherein $R^1$ and $R^2$ are each phenyl, substituted phenyl or cycloalkyl; $R^3$ and $R^4$ are the same or different and are independently selected from H, halo, alkyl or alkoxy;
X is $OCH_2$, $NHCH_2$, $CH_2$ or $CH_2CH_2$; and
Z is $CO_2H$ or tetrazole.

5. The process of claim 3, wherein, in formula I,

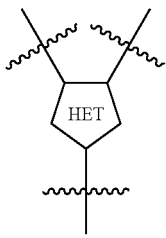

represents

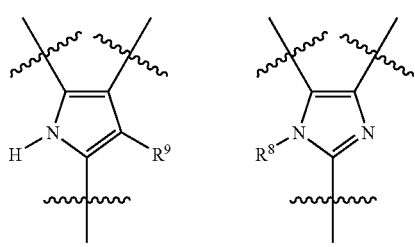

or 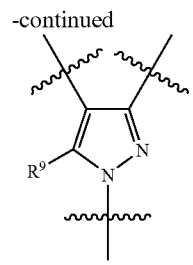

wherein $R^8$ is hydrogen, alkyl or fluoroalkyl;
$R^9$ is hydrogen, alkyl, fluoroalkyl or alkoxy; and
wherein $R^1$ and $R^2$ are each phenyl;
$R^3$ and $R^4$ are each hydrogen;
X is $OCH_2$, $OH_2$ or $NHCH_2$; and
Z is $CO_2H$ or tetrazole.

6. The process of claim 3, wherein said compound of formula I comprises 2'-(5-ethyl-3,4-diphenyl-1H-pyrazol-1-yl)-[1,1']-biphenyl-3-yloxyacetic acid.

7. The process of claim 3, wherein said metal comprises a soft acid.

8. The process of claim 3, wherein said metal comprises palladium.

9. The process of claim 3, wherein said solid extractant comprises a polymer resin.

10. The process of claim 3, wherein said solid extractant comprises a polystyrene resin and said metal binding functionality comprises triphenyl phosphine.

11. A method of recovering a drug substance comprising 2'-(5-ethyl-3,4-diphenyl-1H-pyrazol-1-yl)-[1,1']-biphenyl-3-yloxyacetic acid, or a salt, solvate, stereoisomer, precursor, prodrug ester, or intermediate thereof, from a liquid medium containing said drug substance together with at least one metal, said method comprising
contacting the liquid medium with a solid extractant having a metal-binding functionality, said metal-binding functionality comprising an unsubstituted or substituted phosphine group, said metal-binding functionality being connected to said solid extractant directly or via a linking moiety which does not include at least one of a hydrocarbylsilyl residue or a polyamine residue; and
separating said drug substance from said liquid medium.

12. The method of claim 11, further comprising removing said solid extractant from said liquid medium.

13. The process of claim 11, wherein said metal comprises a soft acid.

14. The process of claim 11, wherein said metal comprises palladium.

15. The process of claim 11, wherein said solid extractant comprises a polystyrene resin and said metal binding functionality comprises triphenyl phosphine.

16. The process of claim 11, wherein said triphenyl phosphine comprises about 0.1 to about 10 mmol per gram of the solid extractant.

17. The process of claim 11, wherein said $PPh_3$ comprises about 0.5 to about 3.5 mmol of the solid extractant.

18. The process of claim 11, wherein the solid extractant is present at about 0.01 to about 10% of the weight of the liquid medium.

19. The process of claim 11, wherein the solid extractant is present at a weight of about 1 to about 4% of the weight of the liquid medium.

20. The process of claim 11, wherein the liquid medium is contacted with the solid extractant at a temperature of about −20° to about 100° C.

21. The process of claim 11, wherein the liquid medium is contacted with the solid extractant at a temperature of about 20° to about 60° C.

22. A method of recovering a drug substance from a liquid medium containing said drug substance together with at least one metal, said method comprising contacting the liquid medium with a solid extractant having a metal-binding functionality, said metal-binding functionality comprising an unsubstituted or substituted phosphine group, said metal-binding functionality being connected to said solid extractant directly or via a linking moiety which does not include at least one of a hydrocarbylsilyl residue or a polyamine residue; and separating said drug substance from said liquid medium, wherein said drug substance comprises a compound of formula I

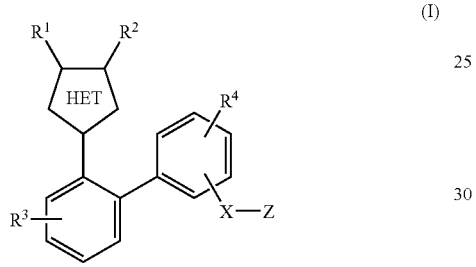

or a salt, solvate, stereoisomer, precursor, prod rug ester, or intermediate thereof, wherein $R^1$ and $R^2$ are the same or different and are independently selected from the group consisting of substituted or unsubstituted aryl, $R^3$ is selected from the group consisting of hydrogen, halogen, substituted or unsubstituted alkyl, substituted or unsubstituted alkenyl, substituted or unsubstituted alkynyl, substituted or unsubstituted heterocyclo, substituted or unsubstituted cycloalkyl, substituted or unsubstituted alkylcarbonyl, polyhaloalkyl, cyano, nitro, hydroxy, substituted or unsubstituted amino, substituted or unsubstituted alkanoyl, substituted or unsubstituted alkylthio, substituted or unsubstituted alkylsulfonyl, substituted or unsubstituted alkoxycarbonyl, substituted or unsubstituted alkylaminocarbonyl, substituted or unsubstituted alkylcarbonylamino, substituted or unsubstituted alkylcarbonyloxy, and substituted or unsubstituted alkylaminosulfonyl;

$R^4$ is selected from hydrogen, halogen, substituted or unsubstituted alkyl, substituted or unsubstituted alkenyl, substituted or unsubstituted alkynyl, substituted or unsubstituted alkoxy, substituted or unsubstituted aryl, substituted or unsubstituted heterocyclo, substituted or unsubstituted aralkyl, substituted or unsubstituted arylalkenyl, substituted or unsubstituted arylalkynyl, substituted or unsubstituted cycloalkyl, substituted or unsubstituted alkylcarbonyl, substituted or unsubstituted arylcarbonyl, polyhaloalkyl, cyano, nitro, hydroxy, substituted or unsubstituted amino, substituted or unsubstituted alkanoyl, substituted or unsubstituted aroyl, substituted or unsubstituted alkylthio, substituted or unsubstituted alkylsulfonyl, substituted or unsubstituted arylsulfonyl, substituted or unsubstituted alkoxycarbonyl, substituted or unsubstituted aryloxycarbonyl, substituted or unsubstituted alkylaminocarbonyl, substituted or unsubstituted arylaminocarbonyl, substituted or unsubstituted alkylcarbonylamino, substituted or unsubstituted alkylcarbonyloxy, substituted or unsubstituted alkylaminosulfonyl, and substituted or unsubstituted arylaminosulfonyl;

$R^1$, $R^2$, $R^3$ and $R^4$ may optionally be substituted with up to 5 substituents selected from the group consisting of hydrogen, halo, alkyl, polyhaloalkyl, alkoxy, polyhaloalkoxy, alkenyl, alkynyl, cycloalkyl, aryl, heterocyclo, aralkyl, arylalkenyl, arylalkynyl, aryloxy, arylazo, hydroxy, nitro, cyano, amino, substituted amino, thiol, alkylthio, arylthio, heterocyclothio, alkylcarbonyl, arylcarbonyl, acyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfinylalkyl, arylsulfonyl, alkylsulfonyl, aminosulfinyl, aminosulfonyl, arylsulfonylamino, heterocyclocarbonylamino, heterocyclosulfinyl, heterocyclosulfonyl, alkylsulfinyl, sulfonamido and sulfonyl;

X represents a valence bond or a divalent linking moiety which can be read from left to right or vice versa and is selected from $(CH_2)_n$, $O(CH_2)_n$, $S(CH_2)_n$, cycloalkylene, $N(R^5)(CH_2)_n$, NHCO, or ethenyl, where n is an integer from 0 to 5, inclusive, and $R^5$ is hydrogen, alkyl, or alkanoyl;

Z is COOR or a tetrazole of the formula

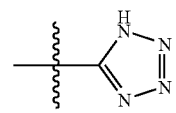

or its tautomer;

wherein R represents a radical selected from the group consisting of H, alkyl, aryl, aralkyl, cycloalkyl, heterocyclo, alkenyl, and alkynyl; and the group

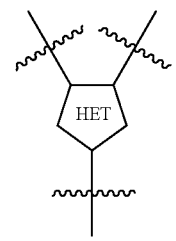

is a 1,2-diazole.

23. The process of claim 22, wherein $R^1$ and $R^2$ are each phenyl or substituted phenyl;

$R^3$ and $R^4$ are the same or different and are independently selected from H, halo, alkyl or alkoxy;

X is $OCH_2$, $NHCH_2$, $CH_2$ or $CH_2CH_2$; and

Z is $CO_2H$ or tetrazole.

24. The process of claim 22, wherein $R^1$ and $R^2$ are each phenyl;
$R^3$ and $R^4$ are each hydrogen;
X is $OCH_2$, $CH_2$ or $NHCH_2$; and
Z is $CO_2H$ or tetrazole.

25. The process of claim 22, wherein said metal comprises a soft acid.

26. The process of clam 22, wherein said metal comprises palladium.

27. The process of claim 22, wherein said solid extractant comprises a polymer resin.

28. The process of claim 22, wherein said solid extractant comprises a polystyrene resin and said metal binding functionality comprises triphenyl phospine.

* * * * *